(12) United States Patent
Dive et al.

(10) Patent No.: US 7,541,157 B2
(45) Date of Patent: Jun. 2, 2009

(54) METHOD OF SCREENING GROUPS OF RADIOACTIVE MOLECULES AND APPLICATIONS THEREOF

(75) Inventors: Vincent Dive, Palaiseau (FR); André Menez, Magny les Hameaux (FR); Reto Stocklin, Bernex (CH); Bertrand Tavitian, Saint Cyr l'Ecole (FR); Fabrice Beau, Massy (FR); Bertrand Czarny, Malakoff (FR); Joël Cotton, Orsay (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/514,562

(22) PCT Filed: May 28, 2003

(86) PCT No.: PCT/FR03/01630

§ 371 (c)(1),
(2), (4) Date: Apr. 17, 2006

(87) PCT Pub. No.: WO03/102579

PCT Pub. Date: Dec. 11, 2003

(65) Prior Publication Data

US 2006/0228296 A1 Oct. 12, 2006

(30) Foreign Application Priority Data

May 31, 2002 (FR) .................................. 02 06698
Jan. 22, 2003 (FR) .................................. 03 00645

(51) Int. Cl.
*G01N 33/53* (2006.01)
*C40B 50/06* (2006.01)

(52) U.S. Cl. ............... 435/7.21; 435/7.1; 435/DIG. 14; 424/9.1; 424/9.34; 424/9.341; 514/2; 514/18

(58) Field of Classification Search ................ 435/7.21, 435/7.1, DIG. 2; 424/9.1, 9.34, 9.341; 514/18, 514/2

See application file for complete search history.

(56) References Cited

U.S. PATENT DOCUMENTS

| 5,753,206 | A | * | 5/1998 | McBride et al. | ............ | 424/1.69 |
| 6,306,365 | B1 | | 10/2001 | Ruoslahti et al. | | |
| 6,403,770 | B1 | * | 6/2002 | Yu et al. | ................. | 530/387.3 |

FOREIGN PATENT DOCUMENTS

WO     01/20331     3/2001

OTHER PUBLICATIONS

Jiracek J. et al: "Development of the First Potent and Selective Inhibitor of the Zincendopeptidase Neurolysin Using a Systematic Approach Based on Combinatorial Chemistry of Phosphinic Peptides" Journal of Biological Chemistry, American Society Biological Chemists, vol. 271, No. 32, pp. 19606-19611, Aug. 9, 1996.
Dive Vincent et al: "RXP 407, a phosphinic peptide, is a potent inhibitor of angiotensin I converting enzyme able to differentiate between its two active sites" Proceedings of the National Academy of Sciences of the United States, vol. 96, No. 8, pp. 4330-4335, Apr. 13, 1999.
Buchardt J. et al: "Solid phase combinatorial library of phosphinic peptides for discovery of matrix metalloproteinase inhibitors" Journal of Combinatorial Chemistry, American Chemical Society, vol. 2, pp. 624-638, Sep. 13, 2000.

* cited by examiner

*Primary Examiner*—T. D. Wessendorf
(74) *Attorney, Agent, or Firm*—Oblon, Spivak, McClelland, Maier & Neustadt, P.C.

(57) ABSTRACT

The invention relates to an amplification-free method of screening groups of radioactive molecules, comprising at least the following steps: (1) the group of molecules is administered to at least one animal; (2) at least one of the animals is slaughtered and the tissue distribution of the radioactivity of the molecules administered is analyzed in vivo; (3) sections of tissue or organs in which a radioactivity signal is detected are selected; (4) radioactive fractions from the sections of tissue or organs are isolated using suitable techniques such as chromatography and/or extraction techniques; and (5) the molecule(s) from the radioactive fractions obtained in step 4 are characterized using suitable analysis techniques such as chromatography and/or mass spectrometry.

11 Claims, 29 Drawing Sheets

Fragments observed in the MS/MS mass spectrum in the case of the peptide propyl-Arg-Phe(PO2-CH2)Leu-AlaNH2

$C_{27}H_{46}N_7O_6P$
Exact mass: 595.32
Molecular weight : 595.67

→ peak A $C_{24}H_{39}N_5O_5P^+$
Exact mass: 508.27
Molecular weight : 508.57

→ peak B $C_9H_{17}N_4O_2^+$
Exact mass: 213.14
Molecular weight : 213.26

→ peak C $C_8H_{10}N^+$
Exact mass: 120.08
Molecular weight : 120.17

→ peak D

Extraction protocol:

METHOD OF SCREENING GROUPS OF RADIOACTIVE MOLECULES AND APPLICATIONS THEREOF

The present invention relates to an amplification-free method of screening libraries of diverse radioactive molecules, to the products of the molecule libraries obtained and to the application of the method in order to identify molecules capable of binding selectively to a particular tissue or a particular organ, that are useful for the development of novel therapeutic compounds, and of contrast agents for medical imaging, and for the screening of medicaments.

In the context of the development of novel medicaments, compounds obtained by chemical synthesis or else derived from the living kingdom (natural substances) are usually evaluated in in vitro tests. The main functions of these screenings are to identify compounds capable of interacting at high affinity with any targets of therapeutic interest (receptors, enzymes, etc.) or else to isolate compounds which are relatively inactive but which will enter into optimization programs. Although these screenings make it possible to detect thousands of very original compounds, only a tiny fraction of them will be the subject of animal studies, an inescapable step for successfully obtaining products that are useful in human health. The fact that, in all these in vitro screening tests, parameters that are essential for the outcome of a substance tested in animals, such as metabolic stability or tissue distribution and elimination properties, are not taken into account, explains in great part the failures of this strategy. The search for better efficiency in the development of substances that are useful in human health requires the development of novel screening methods.

Screening methods comprising a step of in vivo selection have been described. For example, R. PASQUALINI et al. (Nature, 1996, 380, 364-366) describe the injection of mice with libraries of peptides generated by phage display; using this technique, the authors of that article have shown that ligands which bind specifically to certain organs can be identified, after prior amplification. However, the success of this approach depends essentially on the possibility of re-amplifying the few phages which are selected in vivo, in order to have access to the peptide sequences presented by the proteins of the phages selected in vivo.

The method described in that document should, according to its authors, be applicable to libraries based on principles other than that of phage display; in this case, the only requirement is the ability to identify the compound in the tissue after it has bound; however, PASQUALINI et al. specify that, in order to screen chemical molecules, the presence of a tag, allowing an amplification step, such as a nucleic acid sequence, is essential.

The technique defined in the R. PASQUALINI et al. article (Nature, 1996, mentioned above) thus makes it possible to select peptides capable of binding specifically to tumors; for example, when such peptides are coupled to doxorubicin, they increase the effectiveness of this drug with respect to tumors and also reduce its toxicity. Such an application is in particular described in the article by W. Arap et al. (Science, 1998, 279, 377-380).

In PCT international application WO 97/10507, in the name of La Jolla Cancer Research Foundation, the inventors E. RUOSLAHTI and R. PASQUALINI describe a method for obtaining a molecule capable of directing itself specifically to a selected organ or tissue, which method comprises the following steps:
  administering a phage library to an individual,
  collecting or recovering a sample of the organ or of the tissue selected,
  amplifying the phages, and
  identifying a molecule capable of reaching the organ or the tissue selected.

It is specified that said diverse molecules can be linked to a tag, such as a support.

In the context of this PCT international application:
  the term "library" means a collection of molecules, such as organic molecules, peptides, proteins or nucleic acids.
  The tag attached to the molecules constituting the library can be a tag common to several molecules or a specific tag. The tags described in this application are in particular: plastic microbeads, oligonucleotides, bacteriophages or molecules such as biotin or hemagglutinin.

The identification of the molecules which reach their target organ can, for example, be carried out by mass spectrometry, alone or in combination with gas chromatography; high performance liquid chromatography can also be carried out on the target organ, or methods for selective extraction can be used.

By way of example, it is specified that, when the library comprises a population of organic chemical molecules which are bound to specific tags consisting of oligonucleotides, that can be identified by PCR, it is preferable to remove the genomic DNA from the sample in order to reduce "parasitic" PCRs.

It is also specified that, in general, a sufficient number of phages reach the target organ, which effectively makes it possible to identify them after amplification and then to identify the peptide sequence.

More precisely, the examples relate to the screening of a library of phages carrying peptides and the identification of the peptides which reach the brain, the kidney or a tumor.

However, the method described by the team of E. RUOSLAHTI is essentially limited to peptides and has many drawbacks.

In particular:
  the presentation of peptides at the surface of the phages imposes steric and conformational constraints which necessarily impair the interactions between the peptide sequences presented and the potential target. In addition, the poor capacity of the phages to be able to diffuse in various tissues, and also the existence of in vivo elimination mechanisms directed against this type of particles, constitute considerable limitations to the phage display approach;
  it is phages which are identified at the in vivo screening step. However, the binding of a phage does not guarantee that the peptide, having the sequence carried by the phage, will conserve the distribution properties of the phage. This situation is all the more probable if the difference in size between the phage and the peptide alone is considered. Thus, in practice, although a large number of phages can be identified by the screening, there is no guarantee that a single peptide will possess the distribution properties of the phage;
  after extraction of the phages, they must be re-amplified by transfection of bacteria; this constraint introduces an additional step into the method;
  since phages generate many nonspecific interactions, the method described by the group of E. RUOSLAHTI must include several steps of in vivo selection (in general three steps); this makes the method very laborious to carry out and has the drawback that the in vivo screening involves the use of different animals and therefore a variability which can introduce considerable biases;
  this method does not make it possible to take into account the metabolism and the pharmacokinetic (distribution and elimination) data of the compounds, since the in vivo screening step is carried out on the phages and not on the compounds themselves;

this method determines the selectivity of the tissue distribution of the phage selected and not of the peptide itself; this is due to the fact that the group of E. RUOSLAHTI uses antibodies that recognize the phages in order to establish the tissue distribution thereof; there is no other means for monitoring the tissue distribution of the peptides.

Consequently, with regard to these drawbacks, the method described by the group of E. RUOSLAHTI is of limited value in the field of the development of molecules that are useful in human health.

Other methods, also using an in vivo step, have also been proposed:

U.S. Pat. No. 5,770,455 describes a method for synthesizing a product library obtained by combinatorial chemistry. It is specified that these methods constitute a powerful tool for rapidly finding novel ligands.

Several strategies for synthesis by combinatorial chemistry are described (spatially-addressable strategies, split-bead strategies and recombinant strategies) and they differ in terms of the conditions for synthesis: shape of the reaction tubes, type of polymer, control of physical constants (time, temperature, solid-phase or liquid-phase treatment, type of mixture and method for determining the structure of the various members of the library).

The tags proposed in that document are specific for each product ("identifier tag").

It is therefore a method which has the major drawback of being laborious to carry out;

PCT international application WO 99/56789 describes the selection of contrast agents using a library obtained by combinatorial chemistry; more precisely, each product of the library comprises a detectable label; it is specified that only the labels having the desired distribution profile or the desired elimination profile are identified in vivo. The labels must be able to be detected without a sample being taken and without requiring the animal to be sacrificed; the suitable labels are in particular chromophores, heavy atoms, radioactive tags and magnetic particles; however, the library of molecules must contain a plurality of labels which must be able to be distinguished from one another. Despite this specification, this PCT international application WO 99/56789 admits that it is an ideal situation that is difficult to obtain; it is in particular acknowledged that the ratio of different members of the library:different labels should ideally be 1:1, but can be as low as 10 000:1, with ratios of between 1:1 and 1:1000, 1:1 and 1:200, 1:1 and 1:50 and 1:1 and 1:25. In such cases, i.e. when the various members of the library do not all have a unique tag, techniques for indirect detection of the labels are proposed in order to identify the members of the library which correspond to the desired profiles. Moreover, in that application, it is recommended, preferably, to detect the labels in a biological fluid (blood, urine, cerebrospinal fluid, bile, etc.); in this context, the label will preferably be capable of being amplified (oligonucleotide, phage), which implies that it will be best if each member of the library is tagged in a unique manner; this therefore comes back to the techniques disclosed above and to their drawbacks. In that application, the technique described is effectively only applicable in the case of unique tagging with amplification or else using indirect detection techniques, by means of specific binding to receptors.

In all the techniques previously described, the compounds to be screened are coupled with a tag for their subsequent identification; however, the presence of such tags can prevent, by steric hindrance, the interaction of the compound to be screened with its target.

Consequently, the applicant gave itself the aim of providing a method which satisfies the practical needs better than the methods of the prior art, in particular in that it makes it possible:

to select, from a mixture which may contain several thousand compounds, the molecules capable of targeting a tissue or an organ in live animals, by direct analysis of the tissue distribution of the compounds to be screened themselves, and to identify molecules, having specific properties, with a view to their use in medical imaging or else for therapeutic purposes.

According to the library of molecules studied, reference will be made to a library of diverse molecules (obtained by combinatorial chemistry, for example) or a library of biomolecules (in the case of peptide libraries, for example).

More precisely, a subject of the present invention is a method of screening a library of molecules, which comprises:

(1) the administration, to at least one animal, of said library of molecules, in which each molecule is pre-labeled, in particular but not exclusively by replacement of an atom present in said molecule with one of its radioactive isotopes, (2) the sacrifice of at least one of the animals and the analysis of the tissue distribution of the radioactivity of the molecules administered, using sections of tissues or of organs from which samples have been taken, by means of suitable imaging or radio-imaging devices; the radio-imaging devices used are in particular β-imagers, selected according to the radio-active atom to be detected. For example, use may be made of β-imagers which make it possible to detect radiolabeled products that emit β$^-$-particles ($^3$H, $^{14}$C, $^{32}$P, $^{35}$S, $^{125}$I, $^{99}$Tc) or that emit β$^+$-particles ($^{18}$F) present on said tissue or organ sections, (3) the selection of sections of tissues or of organs in which a radioactive signal is detected, (4) the isolation, from said sections of tissues or of organs, selected in step (3), of radio-active fraction by suitable techniques, such as extraction and/or chromatography techniques, and (5) the characterization, using the radioactive fractions obtained in step (4), of said molecule(s) by suitable analytical techniques, such as chromatography and/or mass spectrometry.

As a variant, when this is possible, step (2) comprises the analysis of the tissue distribution of the radioactivity of the molecules administered beforehand to at least one animal, by means of suitable imaging devices, in vitro, using a biological sample extracted and selected beforehand from the group consisting of cells and sections of tissues or of organs. This variant does not therefore require the animal to be sacrificed; it is thus also suitable for use in humans, under conditions which lend themselves well thereto.

For the purpose of the present invention, the term "animal" includes, in accordance with accepted classifications, both nonhuman animals and humans.

According to an advantageous embodiment of the screening method according to the invention, prior to step (2), said method comprises a step (1') for analyzing the tissue distribution of the radioactivity of the molecules administered, by subjecting at least one of the animals to external imaging, in particular by means of detection devices incorporating cameras suitable for detecting the nature of the particles emitted by the radioactive isotope selected ($^{18}$F, $^{11}$C, $^{64}$Cu, $^{76}$Br, $^{124}$I, $^{13}$N, $^{15}$O: positron emission tomography, PET; $^{99m}$Tc, $^{123}$I : gamma-camera).

The in vivo screening of libraries of compounds radiolabeled with tritium means that the animals have to be sacrificed; in fact, detection of the β-electrons from the tritium nucleus can only be carried out using tissue sections since, above a few μm, these electrons are no longer detectable; this explains why step (1') can only be carried out for certain radioactive atoms.

In the course of step (1) of the method according to the invention, each library or group of radioactive molecules is injected into one or more animals, preferably intraperitoneally (I.P.) or intravenously (I.V.); the ability of the various molecules to target a tissue or an organ is then visualized by detecting the radioactivity in the various organs or tissues [steps (1') and (2)]. The modes of detection depend on the nature of the radioactive atom chosen in order to carry out the radiolabeling of the molecules, in particular on the nature of the radiation emitted by the radioactive tracer. The time at which the observation is carried out is a variable parameter.

Step (1') has many advantages:

it makes it possible to carry out a test on live animals and thus to obtain pharmacokinetic data and data regarding the identification of the ligands for which the bioavailability, toxicity and metabolism properties will be compatible with their subsequent use;

it therefore represents a definite advantage compared to the methods comprising only in vitro steps, in particular on cell cultures;

in addition, it makes it possible to rapidly visualize the distribution of the molecules administered and to follow their kinetics; it is thus possible to calculate the kinetics of elimination of the radioactive molecules, so as to determine up until what point the observation can be carried out and what is the best time for carrying out the analysis of the tissues according to step (2). Consequently, the time at which the analysis of the tissue distribution according to step (2) is carried out varies according to the nature of the molecule injected and to its lifetime in the organism. It is thus possible to observe a radioactivity between 10 minutes and 48 hours;

it is based on the detection of sufficiently energetic radiation emitted by certain radioactive atoms; in particular, positron emission tomography (PET) makes it possible to obtain external imaging of the distribution of a compound in all the compartments of an animal, such as the rat or the mouse, or else certain primates.

The invention includes the implementation of the present method:

in its variant in which step (2) comprises the analysis of the tissue distribution of the radioactivity of the molecules administered, by means of suitable imaging devices, in vitro, using a biological sample extracted and selected beforehand from the group consisting of cells and sections of tissues or of organs, and in its variant in which the method comprises a step (1') (in vivo analysis).

In this respect, in humans, the method according to the invention may have a diagnostic aim, when it is used with a library of molecules that has been preselected by means of the method according to the invention carried out, initially, in a nonhuman animal.

According to an advantageous embodiment of the methods according to the invention, in step (2), the tissue distribution of the radioactivity is visualized by means of detection devices incorporating imaging devices suitable for detecting the nature of the particles emitted by the radioactive isotope selected.

The step for analyzing the tissue distribution of the compounds, based on the detection of the radioactivity, makes it possible to rapidly select the libraries or groups according to:

A: The presence or absence of compounds capable of being distributed in the organism.

B: A criterion of selectivity of targeting, if the intention is to identify compounds capable of targeting a particular organ, such as the brain for example.

C: The presence of highly toxic compounds; the library or group is then eliminated or re-synthesized in the form of more discrete mixtures, so as to rapidly eliminate the toxic compounds.

The in vivo selection steps, and more particularly the step (1'), have a double aim:

firstly, to considerably reduce the number of compounds which will be the subject of a subsequent study; in fact, all the molecules that are rapidly eliminated by the organism, or rapidly metabolized and then eliminated, are no longer subsequently taken into consideration;

secondly, for the few compounds that are retained in the organism, to obtain information regarding their tissue distribution and, for example, to center the study only on a particular tissue, such as a tumor.

Steps (3) to (5) concern the chemical identification of the radioactive compounds present in a given tissue or organ. These steps show, first of all, that the radioactivity observed is due only to the presence of molecules present in the starting group.

More particularly, step (4) makes it possible, in particular using suitable chromatographies on a device equipped with a radioactivity detector, to isolate the various fractions containing radioactivity; these fractions are then subjected to mass spectroscopy analysis (step (5)), in order to determine the chemical structure of the radioactive products. This step (5) therefore makes it possible to formally identify whether the product isolated was contained in the starting library or group.

In addition, the combination (i) of a step using a suitable imaging device for more sensitive detection of the radioactive compounds present in a given tissue or organ and (ii) of analytical steps, in particular by mass spectrometry, significantly increases the sensitivity of detection of the method according to the invention compared with methods using only mass spectrometry for both detecting and identifying said compounds.

In other words, the combination of the detection of a radioactive signal (step 2 in particular), prior to the analysis, in particular by mass spectrometry (steps 3 to 5), significantly increases the sensitivity of the detection (of the order of a fentomole ($10^{-15}$M)/mm$^2$). The radioimaging device used is in particular a β-imager, selected according to the radioactive atom to be detected. For example, the β-imager from the company Biospace makes it possible to detect radiolabeled products that emit β$^-$-particles, present on tissue sections at concentrations of the order of a fentomole/mm$^2$, in the case of tritium; this radioimaging device makes it possible to detect various types of radioactive atoms that emit β$^-$-particles, with a detection threshold that is a little lower than that of tritium.

According to the radioactive atom, the following detection thresholds may be defined (counts per minute or cpm):

$^3$H, 0.07 cpm/mm$^2$ $^{35}$S, $^{14}$C, $^{33}$P: 0.01 cpm/mm$^2$ $^{32}$P: 0.1 cpm/mm$^2$.

Thus, the method according to the invention makes it possible to identify compounds having two essential properties: metabolic stability and tissue distribution. These steps make it possible, in particular, to extract the compounds present in the various tissues, with the aim of characterizing their chemical structure. The choice of using radioactive molecules is crucial, since the monitoring of radioactivity constitutes a very sensitive means for monitoring, throughout the extraction, or even purification, steps, the presence of the compounds of interest.

Once the various isolation steps (in particular by extraction) have been carried out, the chemical structure of the compounds is identified by mass spectrometry or any other suitable analytical method, such as HPLC.

More precisely, the radioactive molecules are injected in the form of a mixture, in order to be able to screen a large number of compounds. The intensity of labeling, at a given moment, depends on the affinity of the compound for a particular site, which is modulated by its pharmacokinetics. Thus, the screening experiments are preferably carried out at different moments. This makes it possible to establish the pharmacokinetics and to evaluate the subsequent applications envisioned for these compounds.

According to the observation techniques used for detecting the presence of radioactive molecules in an organ or a tissue, it will be possible:
  either to carry out the analysis on the live animal: in the case of positron-emitting radioactive atoms such as fluorine 18 or γ-ray-emitting technetium 99, using detection devices that incorporate cameras suitable for the detection of this type of radiation,
  or to perform a detection after sacrifice of the animal and to carry out detection of radioactivity using tissue sections.

In all cases, for a fine analysis, at least one animal will be sacrificed.

There is no restriction regarding the types of animals which can be used. In practice, all the animals commonly used in pharmacology may be the subject of a study.

In accordance with the invention, prior to step (1), said library of labeled molecules is prepared by:
  synthesis of a mixture of said molecules via the chemical or enzymatic pathway (L- or D-peptides, pseudopeptides, nucleic acids, lipids, organic compounds) (combinatorial synthesis), and
  labeling of said molecules with radioactive isotopes, such as tritium ($^3$H), carbon 14 ($^{14}$C), iodine 131 ($^{131}$I), iodine 125 ($^{125}$I), phosphorus 32 ($^{32}$P), fluorine 18 ($^{18}$F), sulfur 35 ($^{35}$S), technetium 99 ($^{99}$Tc) or indium 113 ($^{113}$In).

More precisely, the synthesis of large collections of radioactive molecules is carried out by combinatorial synthesis in the case of biopolymers or biomolecules (peptides, pseudopeptides, nucleotides, nucleotide-peptide mixed polymers). The deconvolution approaches (iterative fractionation for separating the various molecules of a mixture), in the case of peptides, described in the literature facilitate the identification of the molecules of interest. Nonpeptide molecules obtained by mass parallel solid-phase synthesis can be used in the method according to the invention, provided that they can be modified with a view to incorporating a radioactive atom.

Since the molecules mentioned above are synthesized in solid phase, the introduction of radioactive atoms is relatively easy. In the case of peptides, for example, the solid-phase synthesis results in a peptide the N-terminal amine end of which can be freed, whereas all the reactive functions carried on the side chains of these polymers are still protected. This property thus makes it possible to very selectively introduce groups carrying radioactive atoms by means of simple acylation of the N-terminal amine function of the polymer still grafted to the solid support, in particular using the numerous radiolabeled derivatives of tritium, that are commercially available, such as succinimide propionate or acetic anhydride, which allow acylation of the amine functions, resulting in the compounds carrying such amine functions being radiolabeled with tritium. Similar compounds make it possible to introduce $^{14}$C by acylation of the amine function. The radiolabeling of peptides with $^{18}$F or with $^{99m}$Tc can be carried out as described, for example, in A. HEPPELER et al. (Curr. Med. Chem., 2000, 7, 971-994).

The syntheses of these biopolymers can also be designed in order to be able to receive, after the in vivo screening steps, a particular radioactive atom. Thus, it is possible to synthesize libraries of peptides in which all the elements incorporate a tyrosine that is iodinated, with nonradioactive iodine, and in which the N-terminal ends are labeled with tritium. After in vivo screening, the molecules of interest may be re-synthesized, but this time incorporating radioactive iodine on the tyrosine. Since the iodinated tyrosine is already present during the screening steps, the final radioactive molecule will necessarily conserve all the biological activity. This example is applicable to various types of biopolymers into which is incorporated a synthon carrying atoms that are nonradioactive, but which, once the screening has been carried out, may be replaced with their radioactive isotopes. Such a strategy applies in particular to technetium 99 or to fluorine 18.

Molecules of natural origin, correctly radiolabeled, can also be screened using the same approach. It is thus possible to screen extracts of microorganisms in which all the molecules are radiolabeled with various radioactive isotopes ($^3$H, $^{14}$C, $^{32}$P, $^{35}$S, for example). A radiolabeled biomass can be obtained when these microorganisms are cultured in the presence of radiolabeled nutrients. Natural extracts, such as venoms (M. TAKEDA et al., Toxicon, 1974, 12, 633-641; E. KOCHVA et al., Toxicon, 1982, 20, 3, 615-636) can be obtained in radiolabeled form on condition that the animal is given radioactive amino acids, in order to allow the incorporation thereof into the toxins produced in the venom gland, for example. Strategies for radiolabeling natural products can be developed in order to mass-produce radiolabeled products that can be used in the screening method according to the invention.

Advantageously, steps (1) to (5) are carried out simultaneously on several animals for which the amounts administered in step (1) are different, and the analysis of the distribution of the radioactivity of the molecules according to step (2) is carried out at different times according to the animal.

Surprisingly, such a method makes it possible to establish the presence of specific interactions between one or more molecules contained in the mixture consisting of the library of molecules and one or more specific site(s) located in an organ or a tissue, without the presence of specific tags, or the need for prior amplification of the compounds.

The method according to the invention has in particular the following advantages:
  it is not limited to peptide sequences, but concerns all types of molecules, in particular molecules obtained by combinatorial chemistry, and especially biopolymers or biomolecules, and also non-peptide molecules and natural substances, in particular plant extracts;
  the radiolabeling does not constitute a constraint since many radiolabeling methods have been described in the literature, as regards various families of compounds obtained by chemical or enzymatic synthesis; in addition, in the case of natural substances, it is possible, according to the type of organisms producing the compounds of interest, to set up strategies which result in the production of bio-synthetic radioactive compounds. Such strategies are based on the introduction of radioactive molecules capable of entering a metabolic cycle of the organism considered. Mention may be made, for example, of the method for radiolabeling peptides as described in M. TAKEDA et al. (mentioned above) or E. KOCHVA et al. (also mentioned above);

the in vivo screening with libraries of small molecules (as opposed to phages), by promoting tissue penetration, allows a much more effective screening of all the receptors present in the organism. Much better exploitation of the molecular diversity contained in the libraries under consideration is therefore possible with this type of screening. The phenomena of clearance eliminating phages from the organism no longer constitute an important limitation;

the chemical identity of the compounds is the same at the various steps of the screening, which is not the case, as specified above, in the method developed by the team of E. RUOSLHATI;

it makes it possible to directly observe the tissue distribution of the compounds to be screened;

it avoids the presence of tags which can prevent, by steric hindrance, the interaction of the product to be screened with its target;

it does not require an amplification step, and it makes it possible to study the metabolism and the pharmacokinetics (distribution and elimination) of the compounds to be screened.

Surprisingly, by combining the radiolabeling of libraries or groups of synthetic products, combinatorial chemistry, techniques for observing radioactivity in animals (nonhuman or human, according to the cases) and methods for isolating (for example extracting) molecules from organs or tissues, allowing them to be analyzed by mass spectrometry or by other suitable analytical methods, it is effectively possible to identify ligands whose bioavailability, toxicity and metabolism properties will be compatible with their subsequent use in an in vivo context, unlike that which is disclosed in the prior art, in which tags more sophisticated than radioactivity are considered to be the only ones that effectively make it possible to detect the tagged molecules. In fact, it is possible to observe a radiolabeled product on a live animal, if use is made of radioactivity emitters of the very energetic type and for which the half-life times are quite short so as not to compromise the life of the animal. This type of tracer is therefore very advantageous, compared with less energetic tracers; however, the short lifetime of these tracers can be incompatible with ex vivo analyses; in this case, tracers with a long lifetime, such as tritium, even though they cannot be used for external observation of the animal, prove to be very advantageous, all the more so since the handling of this type of tracer is relatively nonrestrictive in terms of safety.

Unlike the screenings carried out on isolated organs or cells, the screening comprising a step carried out on the live animal guarantees the functional integrity of the receptors targeted by the ligands, insofar as gene expression is modified in cell culture systems. Finally, compared to the targeting approaches based on the use of antibodies, the method according to the invention can be carried out with molecules of low molecular weight (1000 Da on average). This property, compared to antibodies, implies better tissue penetration and therefore better exploitation of the repertoire of receptors being expressed selectively in a tissue or in an organ.

In addition, given the size of the compounds being investigated, they will not induce an immune response on the part of the host.

According to another advantageous embodiment of the method according to the invention, the isolation of the radioactive molecule(s) associated with said organ(s) according to step (4) is carried out in accordance with the following steps:

removal of the organs in which radioactivity has been detected, grinding of said organs in a suitable buffer, centrifugation of each ground material and recovery of the solution, filtration of the solution, adjustment of the pH, separation by fractions and recovery of the radioactive fractions.

More precisely, in the case of peptides, this isolation step may comprise, after centrifugation of the ground materials, the recovery of the solution and the filtration of the latter:

acidification of the filtrate, passing of the filtrate through a column containing silica grafted with hydrophobic groups allowing the introduction of "reverse-phase" elution techniques; according to the presence of positive or negative charges in the compounds of the library or group, chromatography methods involving ion exchange may advantageously be introduced, collection of the eluate by fractions, and selection of the fractions containing a radioactive substance, concentration under vacuum of the radioactive fractions, filtration through a filtration membrane capable of retaining the products of molecular weights greater than those of the library of origin, concentration of the filtrate, and then analysis of the samples by high pressure chromatography (HPLC) using columns filled with a reverse-phase support; at the outlet of the separating column, the presence of radioactive products is detected using a conventional radioactivity detector.

According to another advantageous embodiment of the method according to the invention, in step (5), the analysis by mass spectrometry is associated with a tandem mass spectrometry analysis (MS/MS).

According to yet another advantageous embodiment of the method according to the invention, the molecules of the library according to step (1) have the following general formula: propyl-$^3$H—NH-Yaa-$_{(R,S)}$Phe(PO$_2$—CH$_2$)$_{(R,S)}$Leu-Yaa'-NH$_2$ in which Yaa and Yaa' represent positions in which the 20 natural amino acids occur.

Such a method finds many applications; mention may in particular be made of:

the development of novel contrast agents for medical imaging; since the compounds screened carry radioactive atoms right from the start, the molecules, once selected, can be directly used to perform medical imaging or else can be modified by the addition of contrast agents that are compatible with in vivo observation by suitable techniques. In this regard, the libraries or groups of tritiated molecules in which all the molecules are carrying a fluorine 19 atom are particularly advantageous. Once the selection has been carried out by in vivo screening, the molecules identified may be synthesized, this time incorporating fluorine 18, thus making it possible to use the molecules as contrast agents for imaging based on the detection of positrons by means of suitable tomographs;

the production of compounds for therapeutic use; in fact, besides their ability to bind to very precise sites in a living organism, some of the molecules identified may have specific biological activities and may thus serve as a basis for the development of therapeutic compounds;

the targeting of medicaments or of any other molecule of interest (delivery to a specific site by chemical coupling of a medicament with a selected molecule). To target a substance of interest to a particular tissue or organ, it is in fact possible to envision chemically coupling this substance of interest to molecules identified by the method according to the invention, and thus being able to deliver it to a tissue space and then a specific site;

the identification of novel receptors that are expressed selectively in a given tissue or organ.

The method according to the invention makes it possible to identify novel receptors that are expressed selectively in a given tissue or organ. This type of information and of identification may be extremely invaluable for developing novel therapeutic strategies. The characterization, in the same step, both of a selective ligand and of its associative selective receptor, not yet identified, represents an invaluable asset for isolating this receptor by developing an affinity column onto which the ligand specific for this receptor is grafted. This same ligand represents a starting structure based on which other ligands may be designed, in particular for the purpose of therapeutic applications.

Such a method therefore also makes it possible to study various pathologies. In fact, pathologies which result in the overexpression of certain receptors, that are hardly expressed, or not at all, in normal individuals, may be readily detected by means of the method according to the invention. Thus, the demonstration of selective labeling between normal and sick animals is extremely useful in terms of diagnosis, of therapy, of imaging and of targeting of medicaments to the affected tissue or organ. This approach concerns, by way of example, the ability to identify chemical compounds capable of binding selectively to a primary or secondary tumor, without labeling the normal tissues or organs of the animal.

It should, in this regard, be noted that injecting normal animals with the same libraries should, by virtue of the difference, be a means for characterizing the expression of receptors specific to a pathology and therefore, by the same token, for revealing markers specific to a given pathology.

Preferably, the synthesis of said molecules or ligands is carried out in solid phase using techniques known in themselves, with the introduction, for example, of a group $CT_3$-$CT_2$-CO in the N-terminal position by acetylation of the $NH_2$-terminal function of the peptides bound to the solid support, using tritiated acetic anhydride.

A subject of the present invention is also a kit for carrying out said screening method according to the invention, characterized in that it comprises:

at least one library of labeled molecules, in which each molecule is prelabeled, in particular but not exclusively by replacement of an atom present in said molecule with one of its radioactive isotopes, means for detecting the radiolabeled products, in particular selected from the group consisting of imaging devices suitable for detecting the radiation to be detected on sections of organs and of tissues, and means for analyzing the detected radiolabeled products, such as: HPLC and/or mass spectrometry.

A subject of the present invention is also a method of identifying and of studying target molecules (or receptors) that are selectively expressed in an organ or a tissue, using a library of molecules, which method comprises:

(1) the administration, to at least one animal, of said library of molecules, in which each molecule is prelabeled, in particular but not exclusively by replacement of an atom present in said molecule with one of its radioactive isotopes, (2) the sacrifice of at least one of the animals and the analysis of the tissue distribution of the radioactivity of the molecules administered, by taking samples of and analyzing sections of various tissues of the animal, by means of suitable imaging devices, as defined above, (3) the selection of sections of tissues or of organs in which radioactivity is detected, (4) the isolation, from said sections of tissues or of organs selected in step (3), of radioactive fractions by suitable analytical techniques, such as extraction and/or chromatography, (5) the characterization, using the radioactive fractions obtained in step (4), of said molecule(s) by suitable analytical techniques, such as chromatography and/or mass spectrometry, (6) the bringing into contact of the molecule(s) obtained in step (5) with a tissue or organ sample that has been selected and taken in accordance with step (2), under conditions that allow binding between the molecule isolated in step (4) and the target molecule and the formation of a complex, and (7) the isolation of said target molecule from said complex.

As a variant, when this is possible, step (2) comprises the analysis of the tissue distribution of the radioactivity of the molecules administered, by means of suitable imaging devices, in vitro, using a biological sample extracted and selected beforehand from the group consisting of cells and sections of tissues or of organs. This variant does not therefore require the animal to be sacrificed.

According to an advantageous embodiment of this method, prior to step (2), said method comprises a step (1') for analyzing the tissue distribution of the radioactivity of the molecules administered, by subjecting at least one of the animals to external imaging, in particular by means of detection devices incorporating cameras suitable for detecting the nature of the particles emitted by the radioactive isotope selected ($^{18}F$, $^{11}C$, $^{64}Cu$, $^{76}Br$, $^{124}I$, $^{13}N$, $^{15}O$: positron emission tomography, PET; $^{99m}Tc$, $^{123}I$: gamma-camera, etc.).

Step (7) of this method in particular makes it possible to study more precisely the properties of the compounds which have been identified. Each molecule selected by means of the in vivo screening is again synthesized, radiolabeled and studied in order to illustrate its tissue distribution capacities, by the same methods which were used for the screening.

A subject of the present invention is a vector for targeting a molecule of interest to a specific tissue space and/or site, characterized in that it comprises a molecule selected by means of the method of screening a library of molecules, as defined above, and for which the tissue distribution to said site has been identified using this method.

A subject of the present invention is also a site-specific composition, characterized in that it comprises (i) a molecule of interest to be targeted to said site, coupled to a molecule specific for said site, the tissue distribution of which has been identified by means of the method for screening a library of molecules, as defined above, and (ii) at least one pharmaceutically acceptable excipient.

A subject of the present invention is also the use of the labeled molecules selected by means of the method of screening a library of molecules, as defined above, for preparing a composition intended to be used in medical imaging.

According to an advantageous embodiment of said use, the labeled molecules are associated with a suitable contrast agent.

A subject of the present invention is also a method of identifying at least one target (for example a receptor) for a molecule of interest, characterized in that it comprises at least:

(1) the coupling of the molecule of interest with a radiolabeled molecule specific for said target, selected by means of the method of screening a library of molecules, as defined above, so as to obtain a radioactive conjugate, (2) the administration, to at least one animal, of the conjugate obtained in step (1), and (3) the in vitro analysis, using a biological sample, of the binding of at least one target of said biological sample with the molecule of interest coupled to said radiolabeled molecule.

A subject of the present invention is also a method of in vivo screening of unlabeled molecules by competition, which method is characterized in that it comprises:

(1) the administration of a labeled molecule for which the tissue distribution has been identified by means of the method of screening a library of molecules, as defined above, to at least one animal, (2) a first analysis of the tissue distribution of the radioactive molecule administered in step (1), by subjecting at least one of the animals to external imaging, in particular by means of detection devices incorporating cameras suitable for detecting the nature of the particles emitted by the radioactiveisotope selected, (3) the administration of a library of unlabeled molecules, (4) a second analysis of the tissue distribution of the radioactive molecule, by subjecting at least one of the animals to external imaging, in particular by means of detection devices incorporating cameras suitable for detecting the nature of the particles emitted by the radioactive isotope selected, (5) the establishment of the kinetics of displacement of the labeled molecule by at least one of the unlabeled molecules, by comparison with the first analysis of distribution of the labeled molecule, and (6) the detection of at least one unlabeled molecule which has shifted the kinetics of the labeled molecule, by iterative fractionation (method of deconvolution) and characterization of said molecule by suitable analytical techniques, such as chromatography and/or mass spectrometry.

As a variant, when this is possible, steps (2) and (4) comprise the analysis of the tissue distribution of the radioactivity of the molecules administered, by means of suitable imaging devices, in vitro, using a biological sample extracted and selected beforehand from the group consisting of cells and sections of tissues and of organs.

A subject of the present invention is also a compound of the library of molecules, of general formula propyl-$^3$H—NH-Yaa-$_{(R,S)}$Phe(PO$_2$—CH$_2$)$_{(R,S)}$Leu-Yaa'-NH$_2$, in which Yaa represents Arg and Yaa' represents Leu, which can be obtained by means of the method of screening a library of molecules, as defined above.

Surprisingly, this compound of formula:

propyl-NH-Arg-Phe(PO$_2$—CH$_2$)Leu-Ala-NH$_2$, which was selected by means of the method according to the invention has in particular the following properties:

it is a potent inhibitor, in vivo, of the zinc peptidases ACE (angiotensin I-converting enzyme) and NEP (neutral endopeptidase or neprilysin) and therefore finds application in cardiovascular pathologies;

it can cross the blood-brain barrier and, consequently, can have the applications as defined above, in particular when it is labeled: (1) in medical imaging, (2) in a method of targeting a molecule of interest, by coupling this molecule of interest to this peptide in the cerebral space, (3) in a method of screening molecules specifically expressed in the brain.

Other phosphinic peptides, of different general formulae, had already been described (French patent application No. 89 14978; French patent application No. 91 05403; French patent application No. 95 01328; French patent application No. 98 08464), some of which (see French patent application No. 98 08464) exhibit inhibitory activity with respect to ACE; however, surprisingly, whereas, according to the prior art, the chemical structures of most compounds that behave as mixed inhibitors of ACE and NEP have a free carboxylate group at their C-terminal end, that is considered to be an essential group for obtaining a strong interaction between the inhibitor and these two peptidases (Bralet et al., Tips, 2001, 22, 3, 106-109; Weber, The Lancet, 2001, 358, 1525-1532; Fink, Exp. Opin. Ther. Patents, 1996, 6, 11, 1147-1164), the compound propyl-NH-Arg-Phe(PO$_2$—CH$_2$)Leu-Ala-NH$_2$ does not comprise such a group, although it effectively exhibits this mixed activity.

Said peptide has the applications as defined above, mainly:
a medicament,
a vector for targeting a molecule of interest, more specifically in the cerebral space,
a site-specific composition in medical imaging,
use in a method of identifying at least one target (a receptor, for example),
use in a method of direct in vivo screening of unlabeled molecules by competition.

More precisely:

a subject of the present invention is also a medicament, characterized in that it comprises at least the compound propyl-NH-Arg-Phe(PO$_2$—CH$_2$)Leu-Ala-NH$_2$ and at least one pharmaceutically acceptable vehicle.

A subject of the present invention is also a vector for targeting or for targeted transfer of a medicament, characterized in that it consists of the compound propyl-NH-Arg-Phe (PO$_2$—CH$_2$)Leu-Ala-NH$_2$.

A subject of the present invention is also the compound as defined above (propyl-NH-Arg-Phe(PO$_2$—CH$_2$)Leu-Ala-NH$_2$), labeled with a radioactive isotope selected from the group consisting of tritium ($^3$H), carbon 14 ($^{14}$C), carbon 11 ($^{11}$C) or phosphorus 32 ($^{32}$P).

A subject of the present invention is a composition intended for medical imaging, characterized in that it comprises the compound as defined above (propyl-NH-Arg-Phe (PO$_2$—CH$_2$)Leu-Ala-NH$_2$), labeled with a radioactive isotope and optionally coupled to another compound, and also at least one pharmaceutically acceptable excipient.

A subject of the present invention is also the use of the labeled compound, as defined above, for preparing a composition intended to be used in medical imaging.

A subject of the present invention is also a method of identifying at least one target for a molecule of interest, as defined above, characterized in that the radiolabeled molecule is the radiolabeled propyl-NH-Arg-Phe(PO$_2$—CH$_2$) Leu-Ala-NH$_2$ peptide.

In this case, the target is preferably located in the cerebral space.

A subject of the present invention is also a method of in vivo screening of unlabeled molecules by competition, as defined above, in which the radiolabeled molecule is the radiolabeled propyl-NH-Arg-Phe(PO$_2$—CH$_2$)Leu-Ala-NH$_2$ peptide.

Besides the provisions above, the invention also comprises other provisions, which will emerge from the following description, which refers to examples of implementation of the method according to the invention and also to the attached drawings, in which:

FIG. 1 illustrates the theoretical distribution of the masses of the library of generic formula propyl-$^3$H—NH-Yaa-$_{(R,S)}$Phe(PO$_2$—CH$_2$)$_{(R,S)}$Leu-Yaa'-NH$_2$, in which Yaa and Yaa' represent positions in which the 20 natural amino acids occur, resulting in the synthesis of 400 different molecules (1600 if the diastereoisomers due to the presence of an asymmetric center at the Phe and Leu residues are counted);

Figure 20:
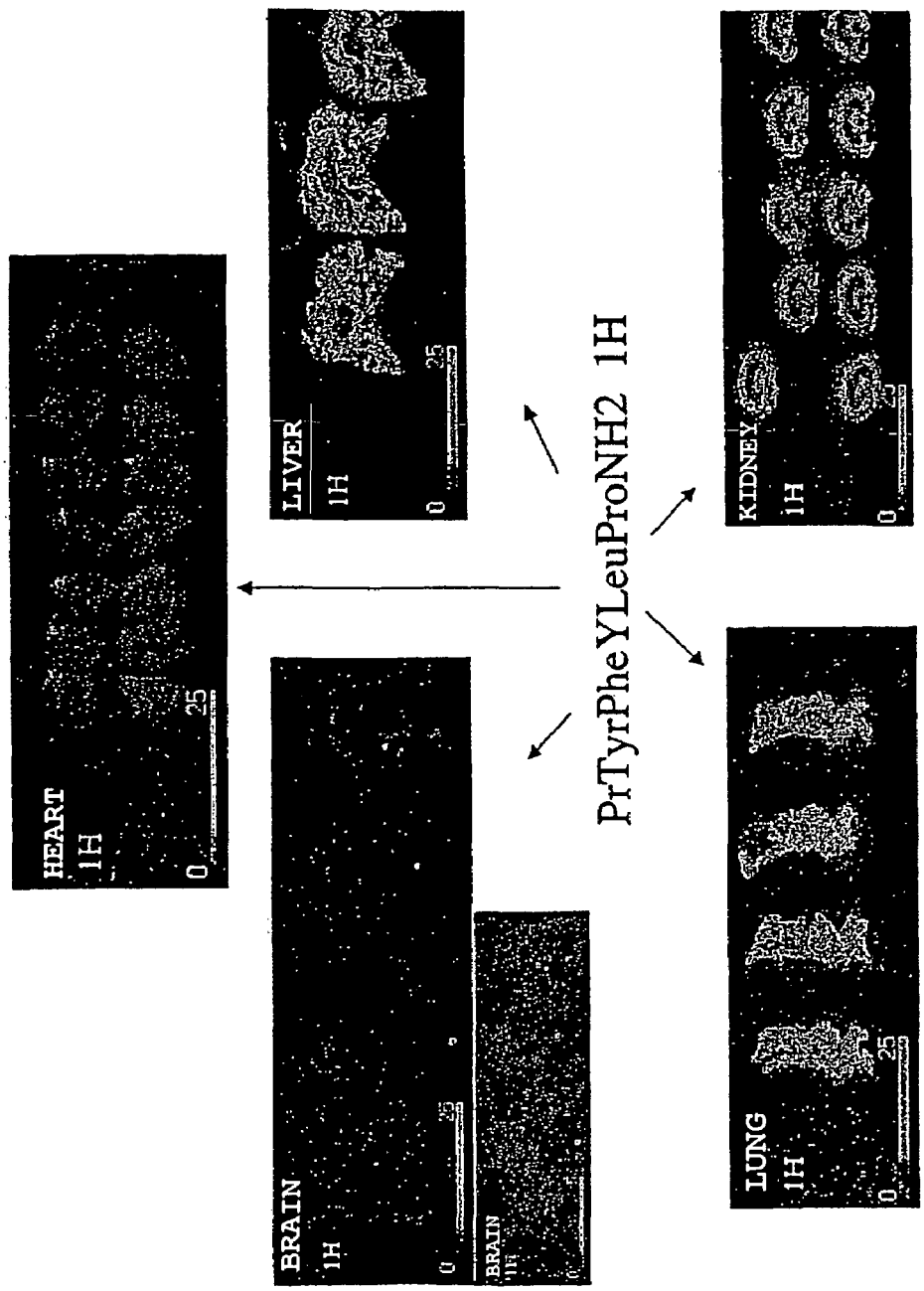
Figure 21:
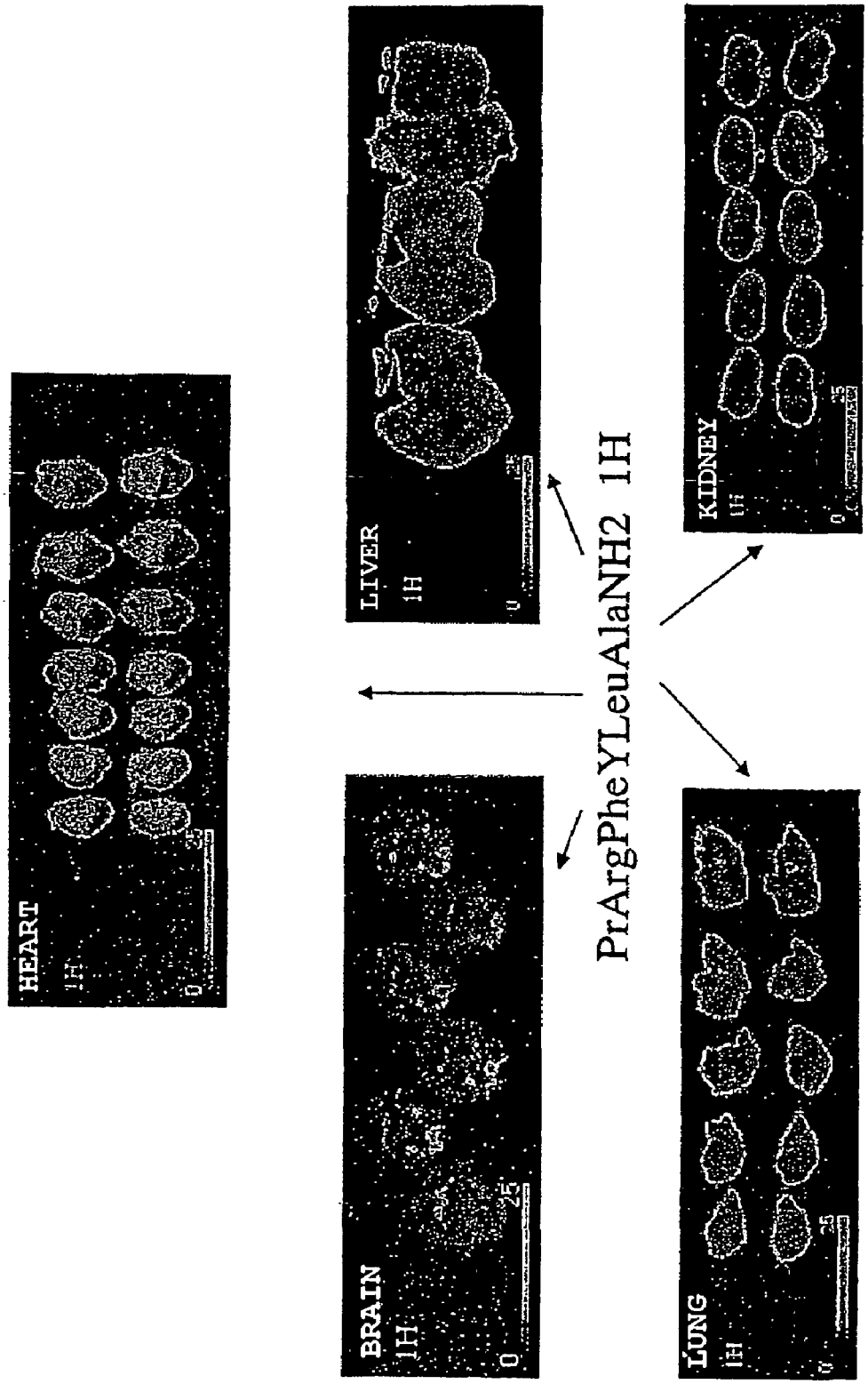
Figure 22:
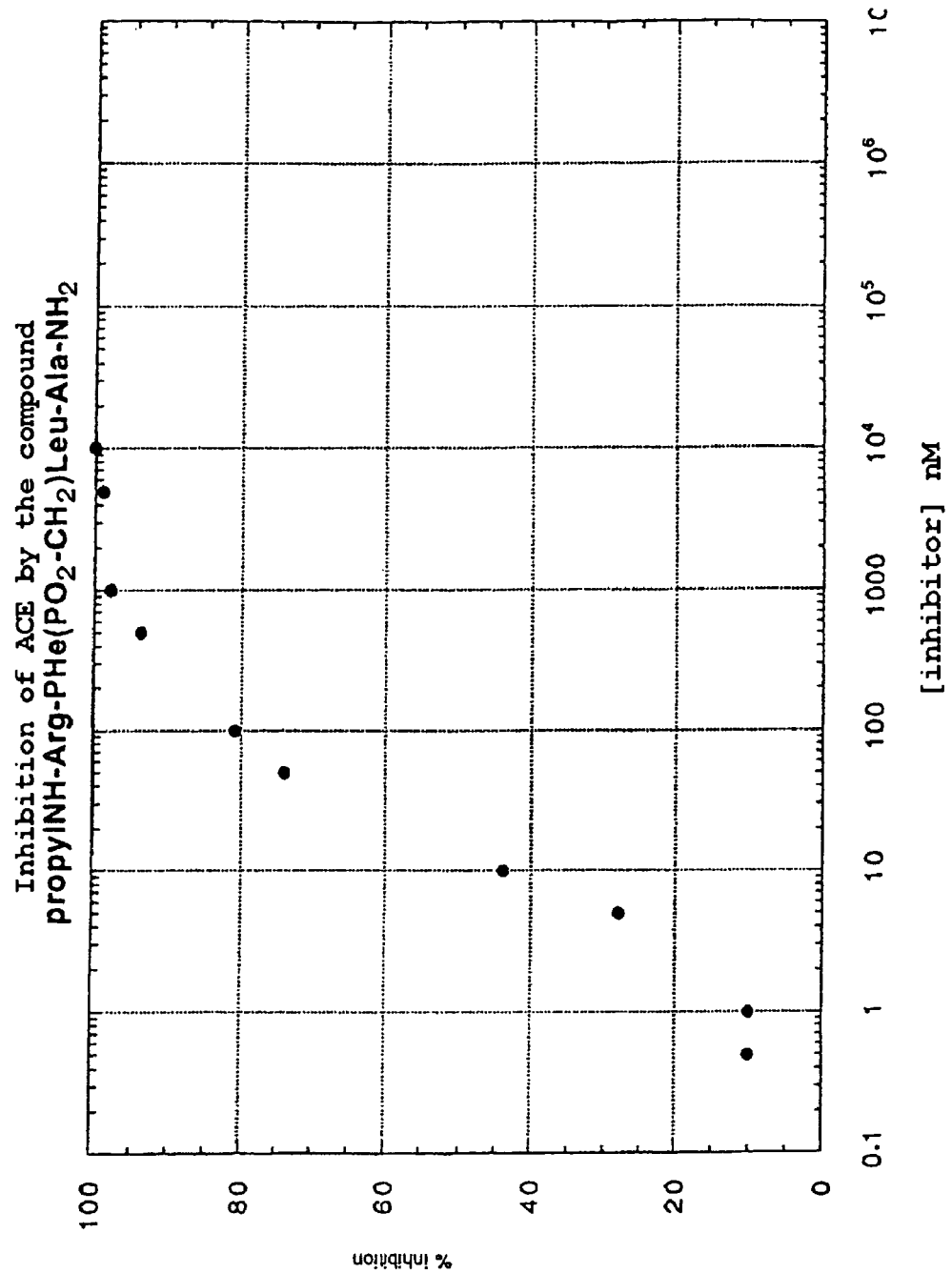
Figure 23:
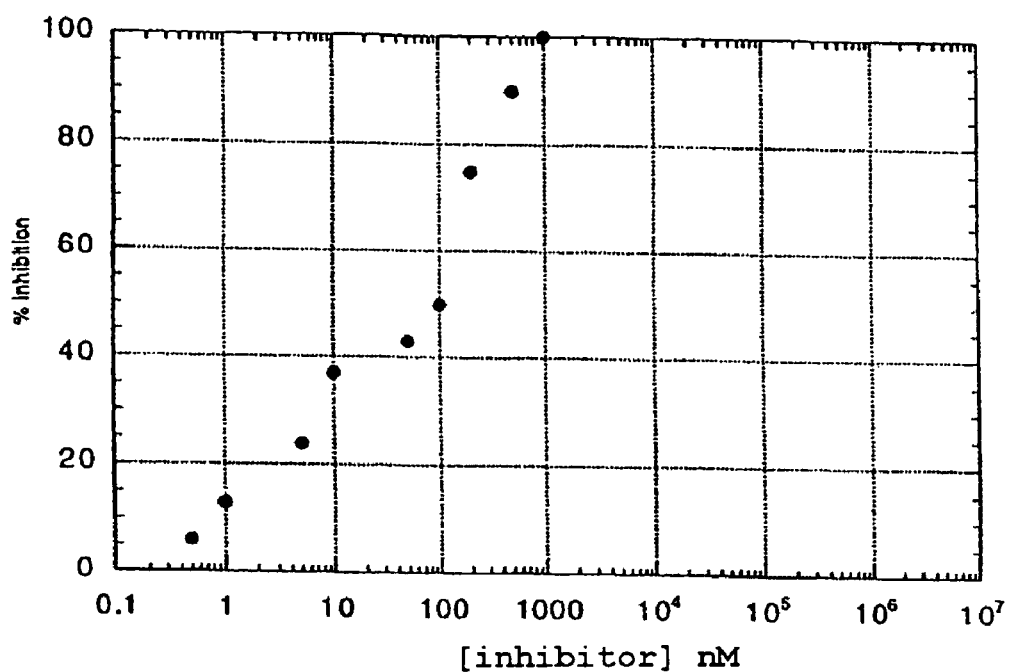
Figure 24:
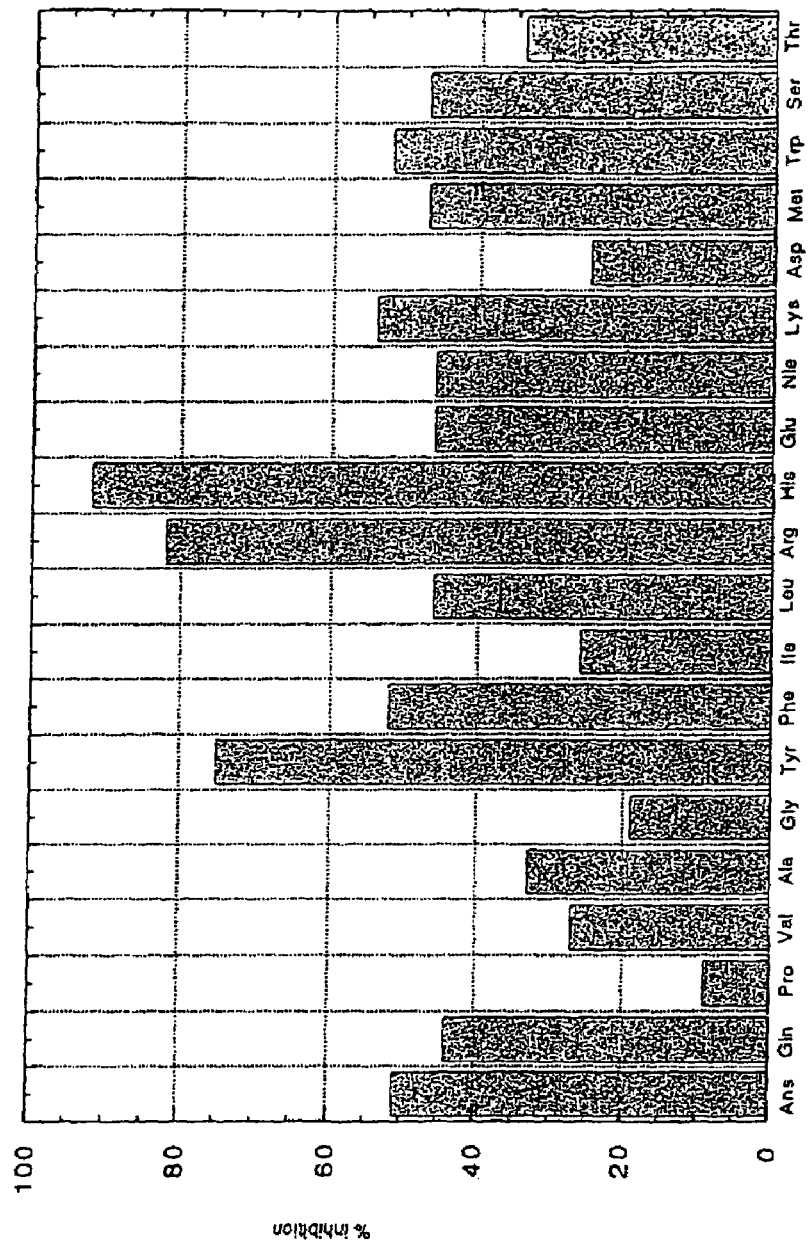
Figure 25:
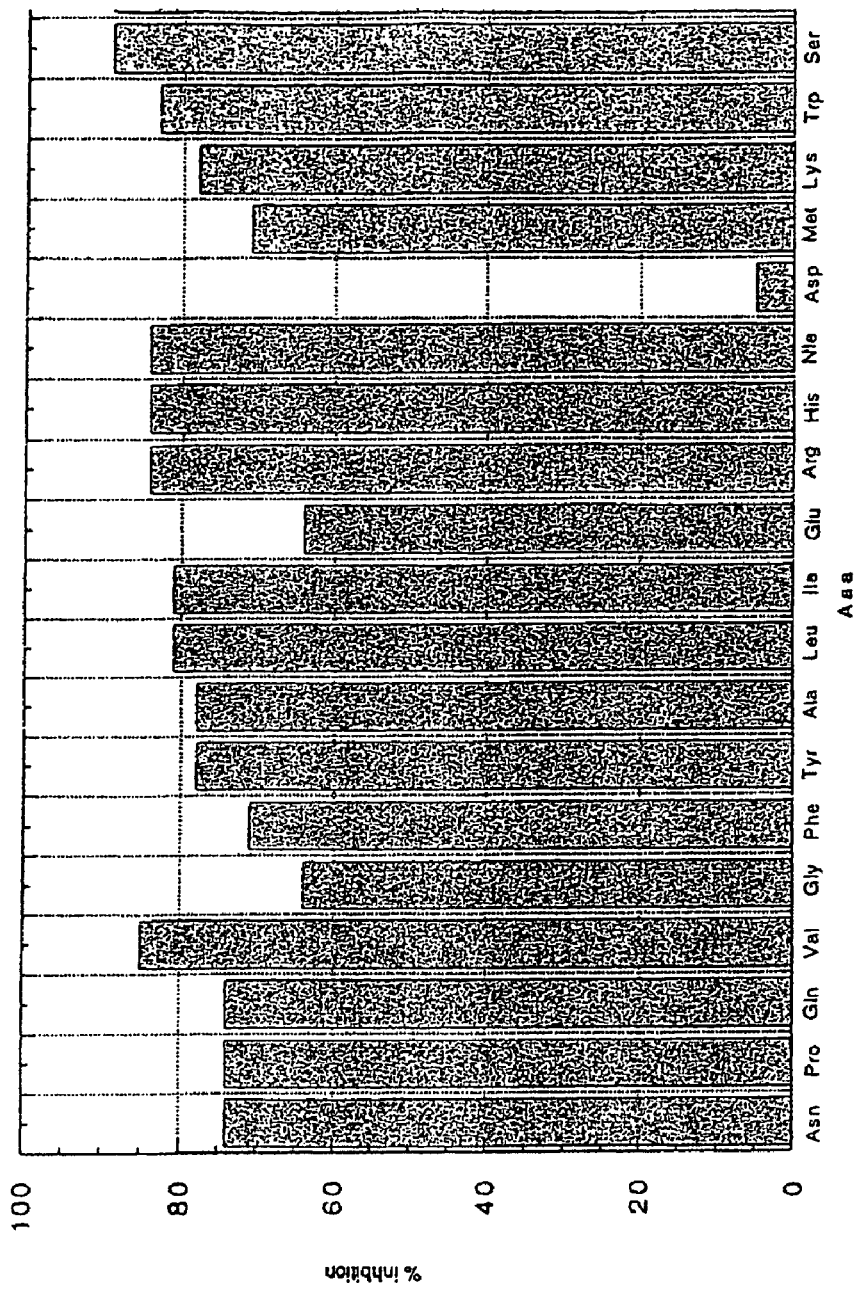
Figure 26:
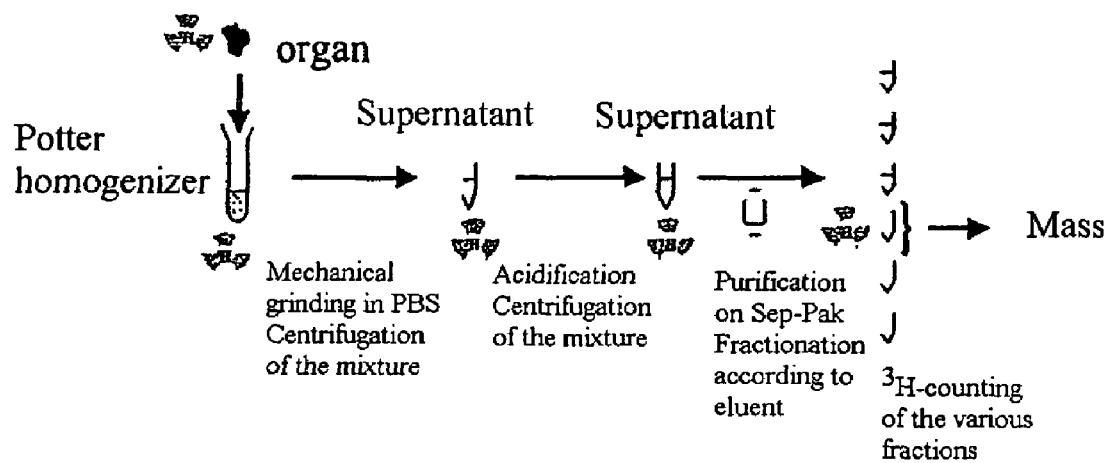
Figure 27:
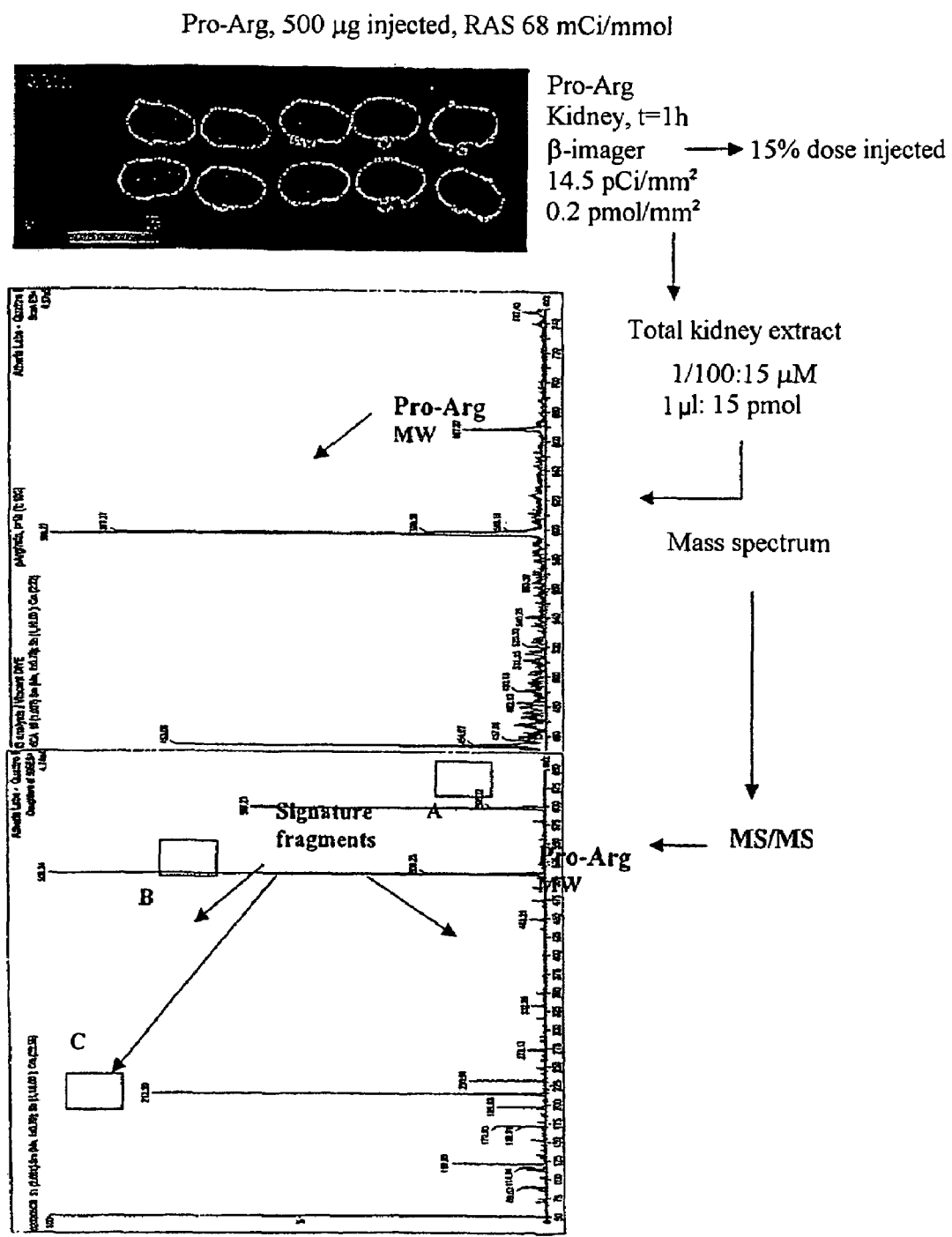
Figure 28:
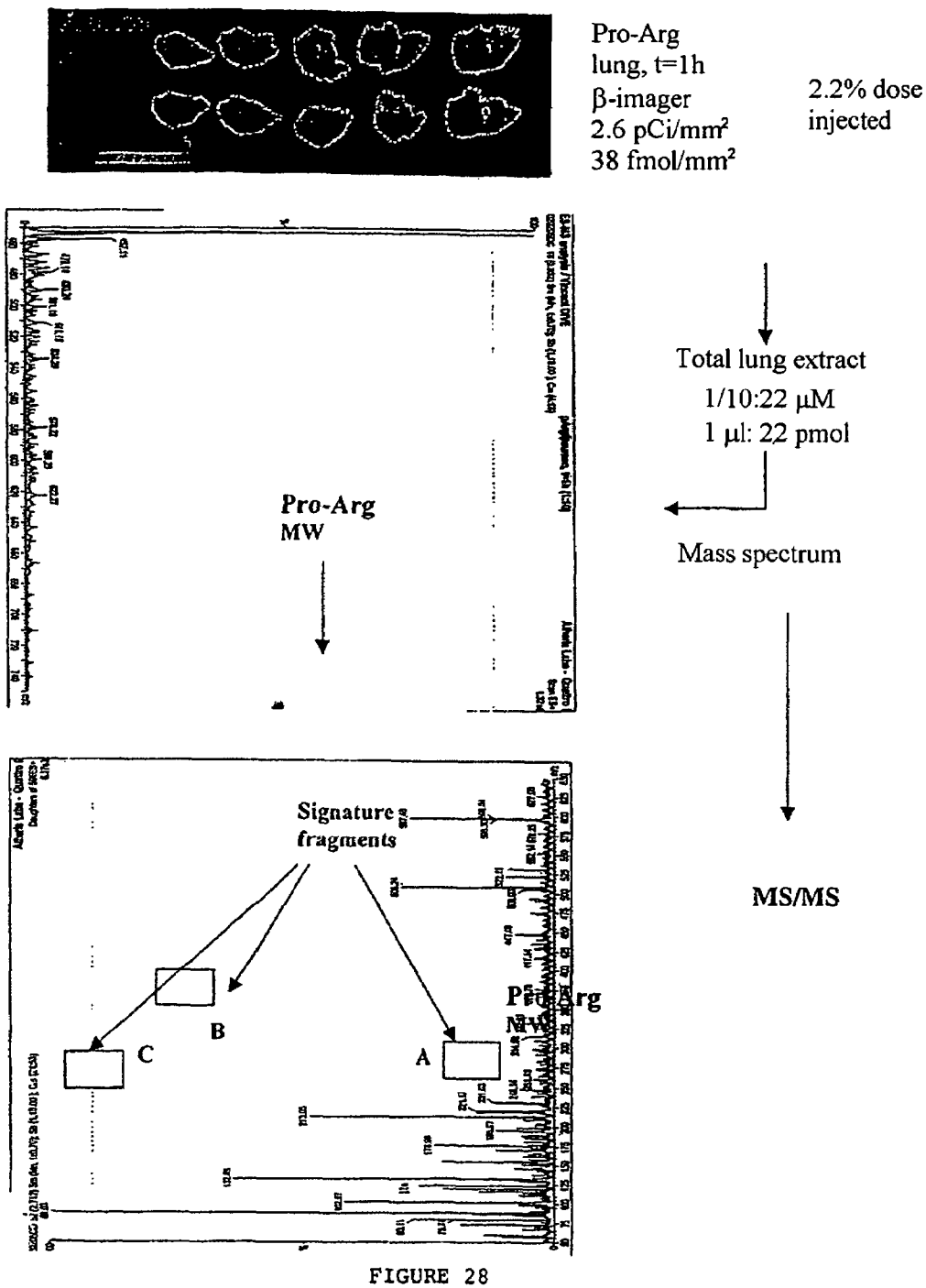
Figure 29:
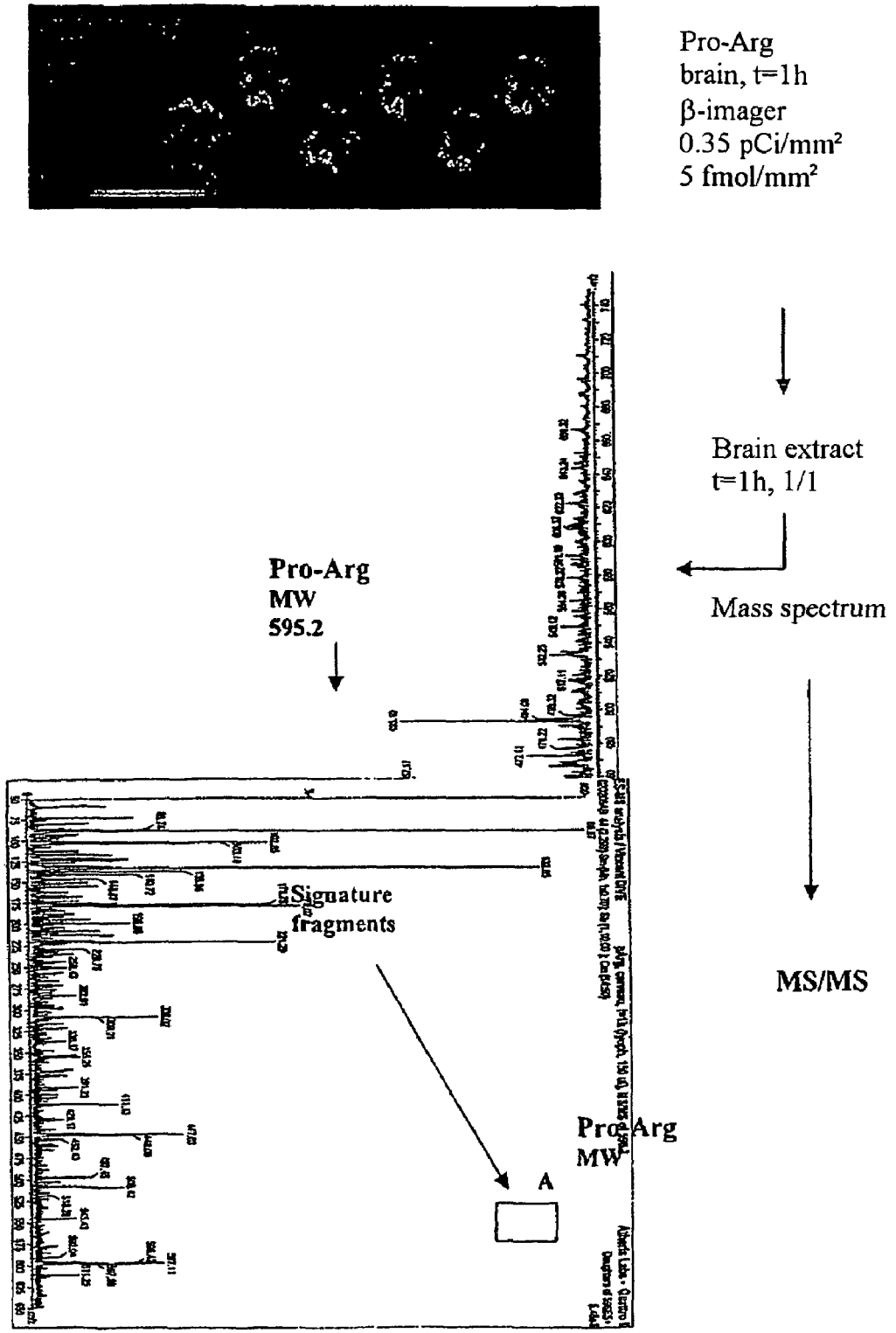

FIG. 20 illustrates autoradiography images of various sections of organs prepared from a mouse that was administered the peptide propyl-$^3$H—NH-Arg-Phe(PO$_2$—CH$_2$)Leu-Ala-NH$_2$ and sacrificed one hour after injection of the product, and FIG. 21 shows autoradiography images of various sections of organs prepared after injecting a mouse with the peptide propyl-$^3$H—NH-Tyr-Phe(PO$_2$—CH$_2$) Leu-Pro-NH$_2$. The animal was sacrificed 1 h after injection of the product;

FIG. 22 illustrates the inhibition of ACE by the compound propyl-NH-Arg-Phe(PO$_2$—CH$_2$)Leu-Ala-NH$_2$;

FIG. 23 illustrates the inhibition of NEP by the compound propyl-NH-Arg-Phe(PO$_2$—CH$_2$)Leu-Ala-NH$_2$;

FIG. 24 illustrates the inhibition of ACE by the sublibraries of generic formula: propyl-NH-Yaa-Phe(PO$_2$—CH$_2$)Leu-Yaa'-NH$_2$ (concentration of each library: 500 nM);

FIG. 25 illustrates the inhibition of NEP by the sublibraries of generic formula: propyl-NH-Yaa-Phe(PO$_2$—CH$_2$)Leu-Yaa'-NH$_2$ (concentration of each library: 250 nM);

FIG. 26 illustrates a protocol for isolating the radiolabeled products by extraction;

FIGS. 27, 28 and 29 illustrate the tissue distribution of the radiolabeled compound propyl-NH-Arg-Phe(PO$_2$—CH$_2$) Leu-Ala-NH$_2$ (pro-Arg) respectively in the kidney, the lung and the brain of the mouse and make it possible to compare the sensitivity of detection of the phosphinic peptide by combining a radioimaging device (β-imager from the company Biospace) and mass spectrometry on this compound (Electrospray, Quatro, MicroMass).

EXAMPLE 1

Library or Group of Phosphinic Pseudo-peptides Radiolabeled with Tritium

Synthesis and Radiolabeling of the Libraries of Phosphinic Pseudopeptides a) Radiolabeling of the Library The synthesis of libraries of phosphinic peptides is based on published protocols (A. Yiotakis et al., J. Org. Chem., 1996, 61, 19, 6601-6605; J. Jiracek et al., J. Biol. Chem., 1995, 270, 37, 21701-21706; J. Jiracek et al., J. Biol. Chem., 1996, 271, 32, 19606-19611; V. DIVE et al., PNAS, 1999, 96, 4330-4335). The library is synthesized on solid phase, using a Rink-amide resin (J. Jiracek et al., J. Biol. Chem., 1996 and V. Dive et al., PNAS, 1999, mentioned above), with a split & combine protocol (J. Jiracek et al., J. Biol. Chem., 1995 and J. Jiracek et al., J. Biol. Chem., 1996, mentioned above). At the end of the synthesis protocol, the generic structure of the peptides on the resin is of the type: Fmoc-NH-Yaa-NH-$_{(R,S)}$Phe(PO(Oad)-CH$_2$)$_{(R,S)}$Leu-Yaa'-CONH—R.

Yaa and Yaa' represent a position substituted with 20 different amino acids, and R represents the resin.

The Fmoc group is cleaved in order to generate a free N-terminal function, allowing the radioactive reactant to be incorporated by acylation of the N-terminal function. The phosphinic peptides were radiolabeled by incorporation onto their free N-terminal function of N-succinimidyl-T5 propionate, a compound which has a specific radioactivity of 97 Ci/mmol. 10.3 nmol of N-succinimidyl-T5 propionate per 16.6 μmol of phosphinic peptides (mean molecular mass of 607, corresponding to 10 mg of final peptide, after deprotection) were incorporated into the peptides, corresponding to an incorporation of radioactivity of 1 mCi per library.

The acylation reaction is completed with cold N-succinimidyl propionate, in excess. After rinsing of the resin, the phosphinic peptides are cleaved by conventional protocols of deprotection and cleavage (J. Jiracek et al., J. Biol. Chem., 1996 and V. Dive et al., PNAS, 1999, mentioned above). The cleavage solvents are eliminated by successive rounds of evaporation. The peptides brought to dryness are taken up in 50 μl of DMSO, 15 μl of 1M NaHCO$_3$ and 50 μl of PBS. The pH of the solution is adjusted to 7 with the 1M NaHCO$_3$ solution. The final volume is adjusted to 500 μl with PBS. This solution is used for the injection administered to the animals. The mass spectrum of the library (FIG. 2), and also various MS/MS fragmentation experiments on this library, show that there is a very good representation of all the compounds theoretically expected.

b) Characteristics of the Library Obtained

Libraries of phosphinic peptides radiolabeled with tritium are thus obtained. The generic formula of the library synthesized according to the protocol defined above is propyl-$^3$H—NH-Yaa$_{(R,S)}$Phe(PO$_2$—CH$_2$)$_{(R,S)}$Leu-Yaa'-NH$_2$, in which Yaa and Yaa' represent a position in which an equimolar mixture of 20 amino acids occurs. This library therefore comprises 400 compounds, officially 1600 if the presence of two asymmetric centers in these structures is taken into account. The compounds were radiolabeled on the N-terminal end by incorporation of tritiated propyl acid of the type C$^3$H$_3^-$C$^3$H$_2$—COOH, incorporating five tritium atoms in its structure.

Figure 1:
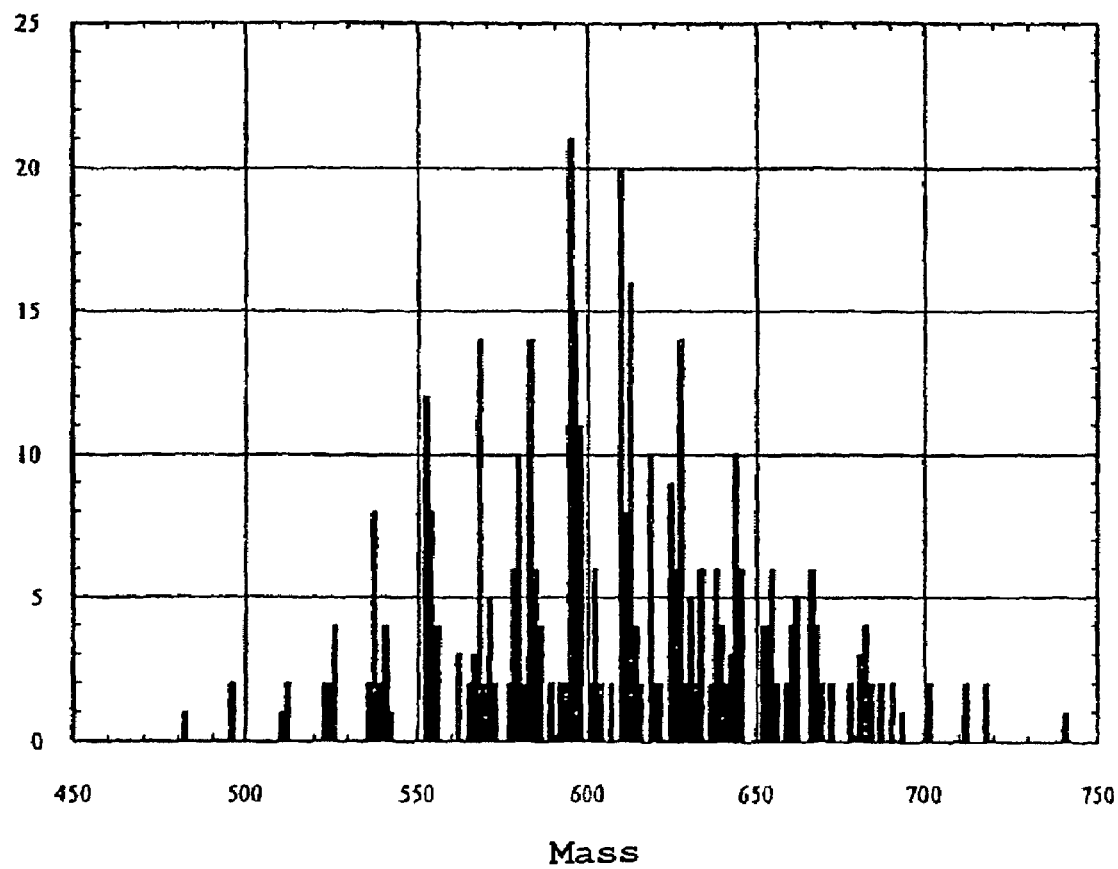

FIG. 1 illustrates the theoretical distribution of the masses of the library of generic formula propyl-NH-Yaa$_{(R,S)}$Phe(PO$_2$—CH$_2$)$_{(R,S)}$Leu-Yaa'-NH$_2$.

A theoretical envelope corresponding to the masses of the various phosphinic peptides contained in the library is represented in this figure. It is noted that this envelope is not continuous, but consists of distinct unresolved peaks, reflecting a distribution by group of the various masses of the products of this library.

Figure 2:
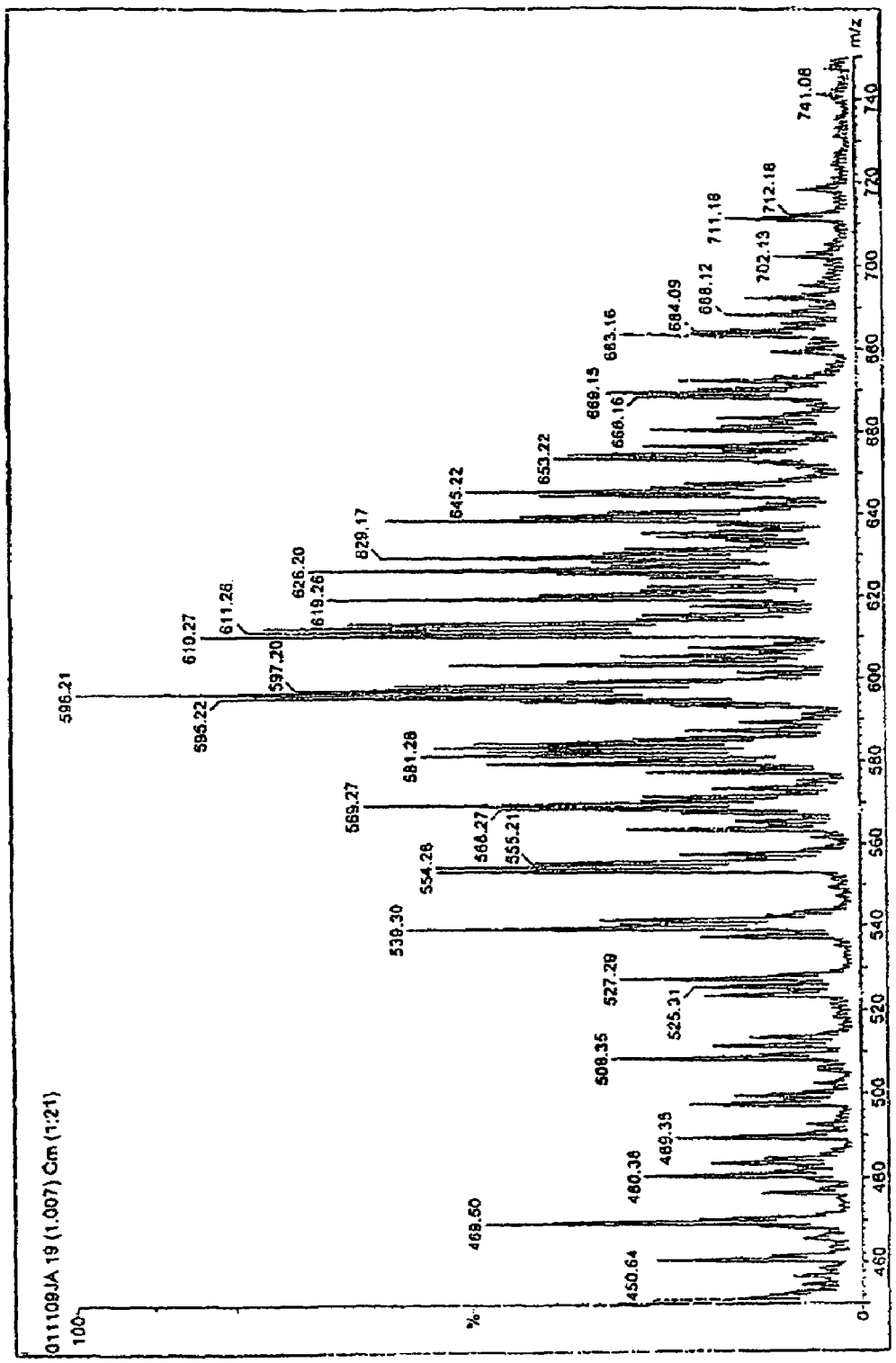
FIG. 2 represents the experimental mass spectrum of the library of generic formula propyl-$^3$H—NH-Yaa-$_{(R,S)}$Phe(PO$_2$—CH$_2$)$_{(R,S)}$Leu-Yaa'-NH$_2$.

FIG. 2 illustrates the experimental mass spectrum (ES-MS=Electro Spray Mass Spectroscopy) of the library of generic formula propyl-NH-Yaa$_{(R,S)}$Phe(PO$_2$—CH$_2$)$_{(R,S)}$Leu-Yaa'-NH$_2$.

When the theoretical envelope (FIG. 1) is compared with the experimental mass spectrum corresponding to the library (FIG. 2), it is noted that the theoretical data correspond very well with the experimental data. This agreement indicates that all the phosphinic peptides are very well represented in this library. The MS/MS experiments for fragmentation of the peaks observed in the MS spectrum make it possible to show the existence of the phosphinic peptides theoretically expected in this library.

Characterization of the Phosphinic Peptides by Mass Spectrometry:

The choice of a protective group of type CH$_3$—CH$_2$—CO, rather than the one conventionally used in peptide chemistry, CH$_3$—CO, was found to be useful in the characterization of the molecules by mass spectrometry. Each phosphinic peptide in this library is characterized by the nature of the amino acid residues present, respectively, in the N- and C-terminal positions. This library is characterized by the presence of pairs of peptides, which have exactly the same mass and the same amino acid content, only their sequence varying, as illustrated below:

for example, the following two peptides cannot be distinguished from one another according to their mass, which is identical:

Propyl-Asp-Phe (PO$_2$—CH$_2$)Leu-Ala-NH$_2$

Propyl-Ala-Phe (PO$_2$—CH$_2$)Leu-Asp-NH$_2$

The MS/MS fragmentation techniques carried out on a certain number of phosphinic peptides make it possible to conclude that it is possible to unambiguously identify the chemical structure of the compounds, even when at least two peptides correspond to the same mass. This property is due to the mode of fragmentation of this type of phosphinic peptide, which makes it possible in particular to identify the nature of the residue in the N-terminal position.

Figure 3:
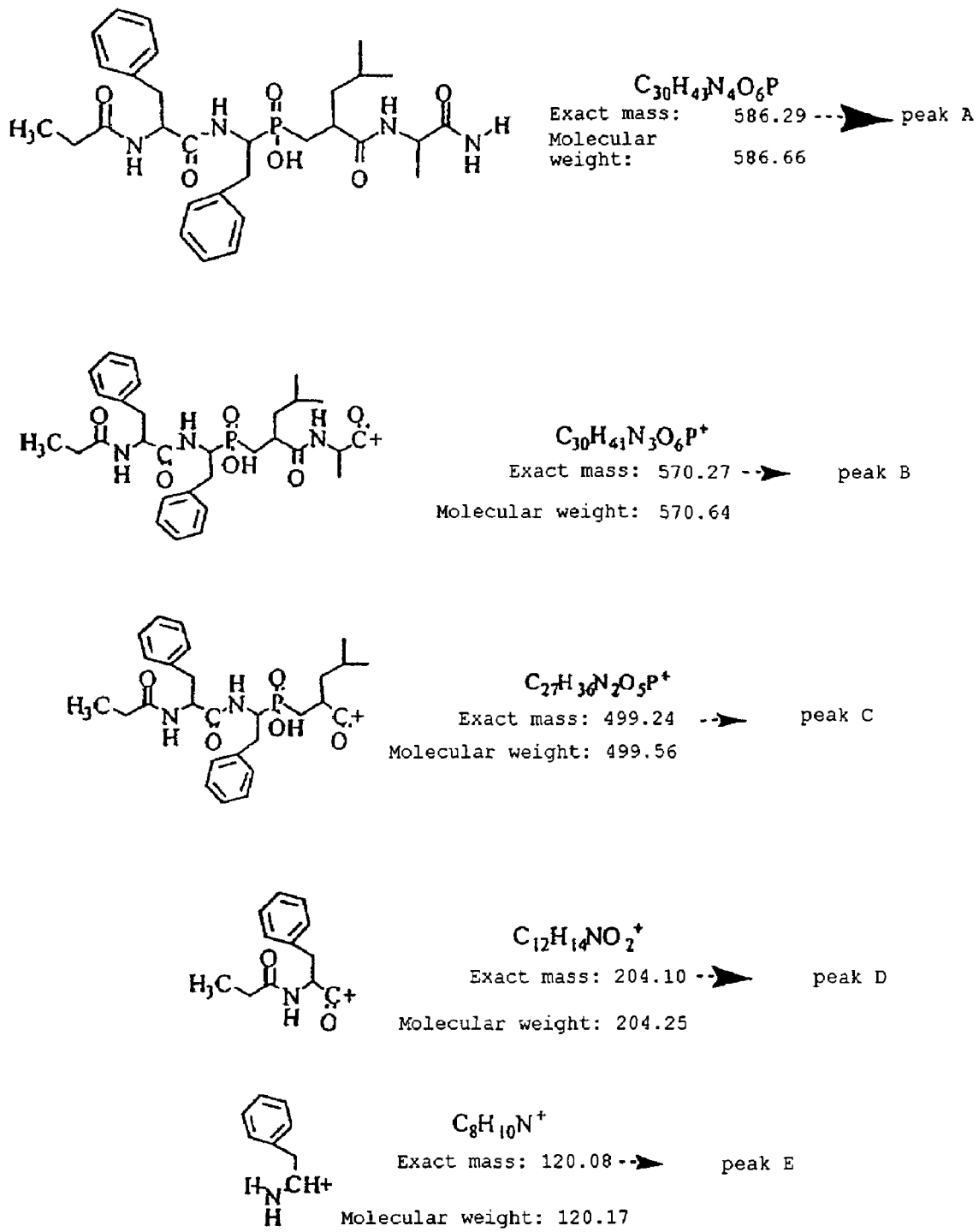
FIG. 3 represents an example of the chemical structures observed in the MS/MS spectra during the fragmentation of the phosphinic peptide propyl-$^3$H-Phe-Phe(PO$_2$—CH$_2$)Leu-Ala-NH$_2$ (selection of the compound of mass at 595)

FIG. 3 illustrates an example of the chemical structures observed in the MS/MS spectra when the phosphinic peptide propyl-Phe-Phe(PO$_2$—CH$_2$)Leu-Ala-NH$_2$ is fragmented.

Figure 4:
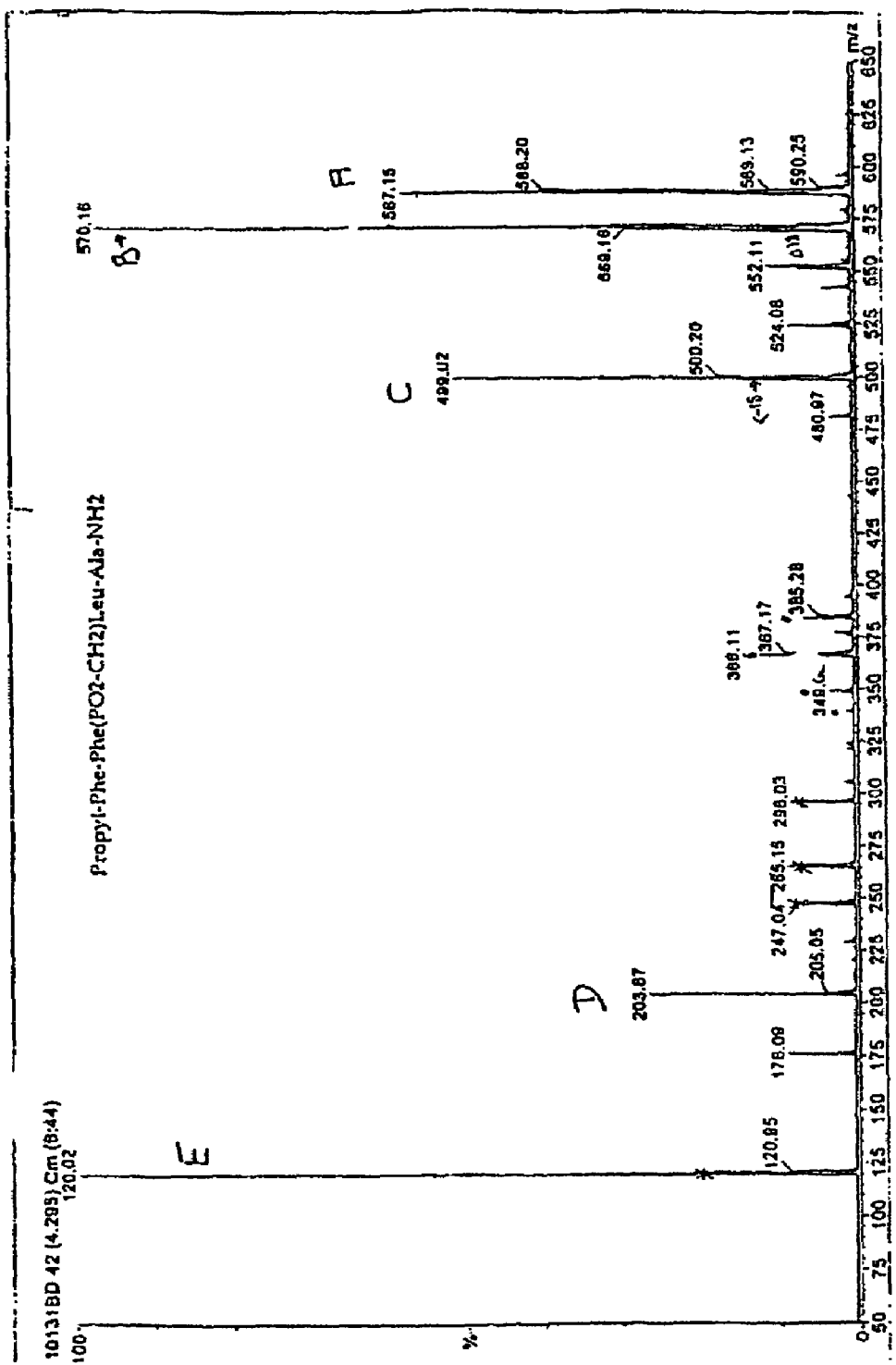
FIG. 4 illustrates the MS/MS spectrum of the peptide propyl-$^3$H-Phe-Phe(PO$_2$—CH$_2$)Leu-Ala-NH$_2$.

FIG. 4 illustrates the MS/MS spectrum of the peptide propyl-Phe-Phe(PO$_2$—CH$_2$)Leu-Ala-NH$_2$.

As illustrated in these FIGS. 3 and 4, the residue in the N-terminal position always appears in the form of an entity bearing the propoxide group (pro-Phe-CO$^+$, peak D of FIGS. 3 and 4). Observation of this entity in the MS/MS spectra therefore makes it possible, in most cases, to determine the nature of the amino acid at the N-terminal position of the peptide and, consequently, that of the residue in the C-terminal position, the mass of the peptide being known. Another species is also systematically observed (pro-Phe-Phe(PO$_2$—CH$_2$)Leu CO$^+$, peak C of FIGS. 3 and 4); the observation thereof corroborates the nature of the residue at the N-terminal position of the sequence (Phe residue in the example).

These characteristics of the mode of fragmentation of the phosphinic peptides present in this library come from the introduction of the propoxide group. By virtue of these characteristics, it is also possible to identify the chemical structure of the compounds, even in cases where several phosphinic peptides correspond to the same mass.

The presence of a peak at mass 120 in the MS/MS spectra when the phosphinic peptides are fragmented (peak E of FIGS. 3 and 4) will be noted. The observation of this peak, which is characteristic of a phosphinic peptide, is very useful for detecting the presence of a phosphinic peptide in organ extracts.

Injection of the Library into Animals and Observation of the Tissue Distribution of the Tritiated Peptides a) Injection of the Libraries Obtained into Animals The mice used for the experiments are female Balb/C mice. The phosphinic peptides of the library (10 mg, radioactivity ranging from 0.8 to 1 mCi) are solubilized in a solution of PBS containing 10% of DMSO. If the presence of 400 molecules in this library is considered, the amount of each product injected is of the order of 25 µg per animal, representing a dose of 1.25 mg/kg for mice weighing 20 g. In the case of injection of a single product, the doses used were 20 mg/kg, for a total radioactivity ranging from 100 to 150 µCi. The injections were given at various times (5 min, 1 h, 3 h and 24 h).

b) Preparation of the Organ Sections

Immediately after the animals had been sacrificed, the various organs or tissues are removed, rinsed in a PBS solution and immersed in heptane cooled to −70° C. (eutectic mixture of heptane and dry ice). The frozen tissue sections, 25 µm thick, are prepared by means of a microtome at −20° C. After drying, the sections are analyzed in a β-imager.

c) Results

Analysis of the Sections in a β-Imager

The libraries of radiolabeled phosphinic peptides are injected intraperitoneally into mice, in accordance with the protocol described above.

Figure 5:
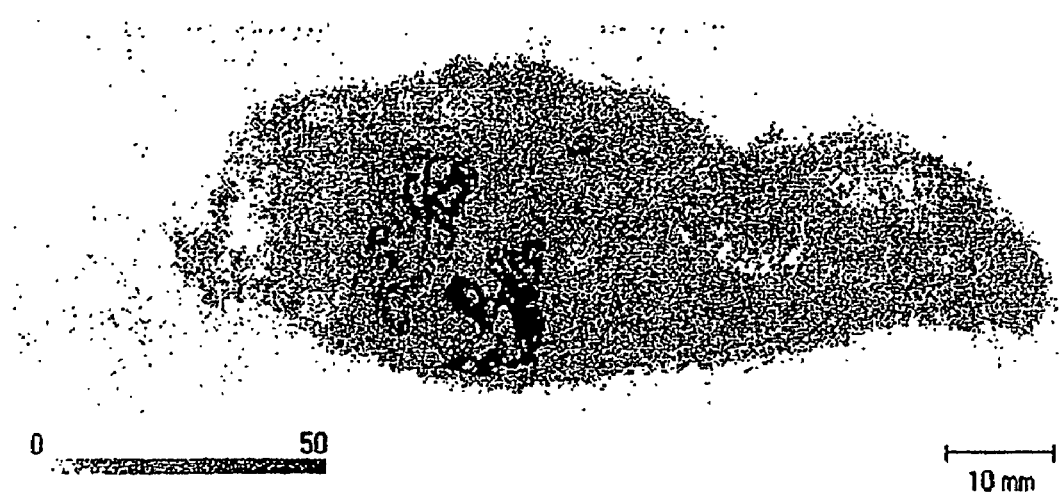
FIG. 5 represents an autoradiograph, prepared on a β-imager, of a sagittal section of the whole body of a mouse that was administered a solution containing a library of phosphinic peptides corresponding to the generic formula propyl-$^3$H—NH-Yaa-$_{(R,S)}$Phe(PO$_2$—CH$_2$)$_{(R,S)}$Leu-Yaa'-NH$_2$, the animal having been sacrificed 1 h after the injection.

After a certain period of time (1 h or 15 min), the animals are sacrificed. Whole body sections are prepared and analyzed by autoradiography on a β-imager, a device capable of detecting the β-radiation of tritium. These experiments indicate, both at 15 min and 1 h after injection of the library, that radioactivity is observed in various organs; FIG. 5 illustrates an autoradiograph, produced on a β-imager, of a sagittal section of the whole body of a mouse which was administered a solution containing the library of phosphinic peptides and which was sacrificed 1 h after the injection.

Other than in the liver and the kidney, radioactivity is observed in the heart and the lungs, for example. Furthermore, experiments in which the animals were subsequently sacrificed confirm that this library does not possess any compounds that induce mortality or toxicity in the animals for the observation periods carried out. It can therefore be concluded that, during these experiments, the vital functions of the animals were preserved. This aspect is important since it guarantees that the compounds identified should interact with "receptors" that are physiologically expressed.

Extraction of the Phosphinic Peptides:

a) Protocol

The organs are rapidly removed after the animal has been sacrificed and are placed in a PBS solution at 4° C. A few minutes later, the organs are transferred into a Potter homogenizer containing 2 ml of PBS at 4° C., and are then ground manually. The ground material is transferred into a centrifuge tube containing 15 ml of PBS. After centrifugation for 30 min at 4000 rpm, the upper phase is separated from the cell pellet and passed through 0.45 µm filters. This filtrate, after having been acidified, is loaded onto a cartridge containing 5 g of C18 phase, this cartridge having been rinsed beforehand in an aqueous solution containing 0.1% of TFA.

The elution protocol consists in first passing through 20 ml of water containing 0.1% of TFA, and then 30 ml of an aqueous solution containing 50% of acetonitrile and 0.1% of TFA, and then 20 ml of an aqueous solution containing 80% of acetonitrile and 0.1% of TFA.

The eluate leaving the C18 cartridge is collected in 2 ml fractions. A radioactivity count makes it possible to identify the fractions containing radiolabeled phosphinic peptides.

The radioactive fractions are concentrated under vacuum and the products are taken up in water, and then the various solutions are passed over a filtration membrane that retains products having a molecular weight above 5000 Da. The solution thus filtered is concentrated under vacuum to a volume of 100 µl.

These samples are then ready to be analyzed, either by high performance chromatography coupled to a system for detecting radioactivity in order to observe the radioactive phosphinic peptides, or by mass spectrometry.

This step reveals the presence of phosphinic derivatives, contained in the starting library, capable of being distributed in certain organs. In order to be in a position to identify the phosphinic derivatives retained in these organs, various protocols for extracting the phosphinic derivatives were tested, using in particular detection of the radioactivity, as specified above, in order to monitor the presence of the compounds of the library throughout the steps of the extraction procedure. Use of the fractionation protocol made it possible to analyze these extracts both by HPLC coupled to detection of radioactivity and by mass spectrometry. Optimal use of mass spectrometry, in particular the sensitivity of the method, is based on the quality of the samples which will be subjected to the analysis. The protocols for preparing the samples are therefore extremely important in this step, but can vary according to the chemical functions carried by the products of the library. For example, in the case of the phosphinic pseudopeptides, after rinsing with $H_2O$ containing 0.1% TFA, all the phosphinic pseudopeptides of the library can be eluted with 50% $CH_3CN$, whereas at 80% $CH_3CN$, many endogenous products, which can interfere with the subsequent analyses, are eluted.

b) Analysis of the Mass Spectra of Organ Extracts Derived from Animals Having Been Given the Library of Phosphinic Peptides by i.p. Injection The analysis of the mass spectra of the various extracts prepared from various organs and tissues (kidney, liver, lung, heart, brain, tumor) indicate that, other than in the kidney, no signal specific to the phosphinic peptides appears in the mass spectra of these various extracts.

Figure 6:
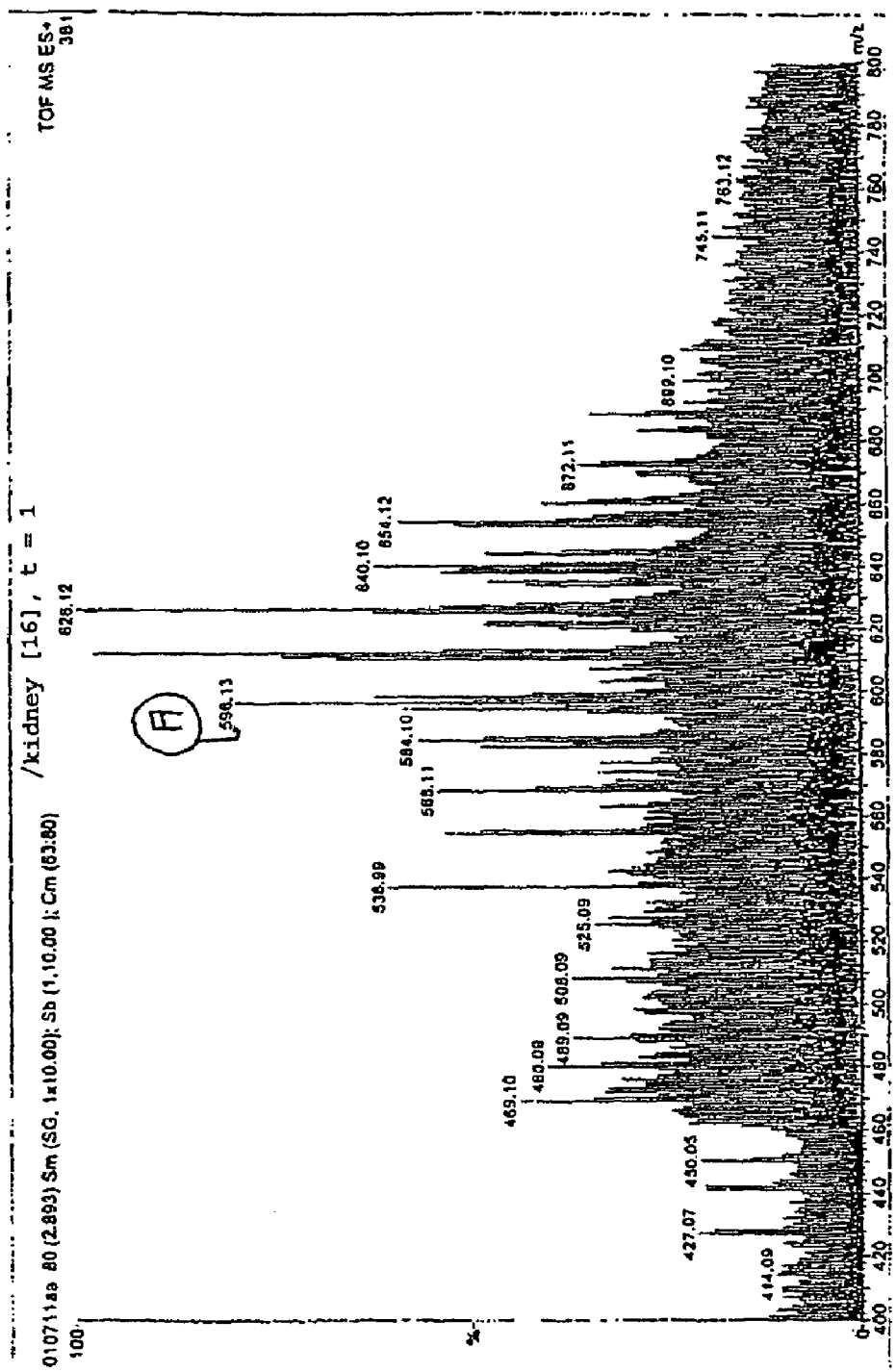
FIGS. 6 to 8 represent mass spectra of various organ (kidney, lung and heart) extracts after I.P. injection of the library of phosphinic peptides.
Figure 7:
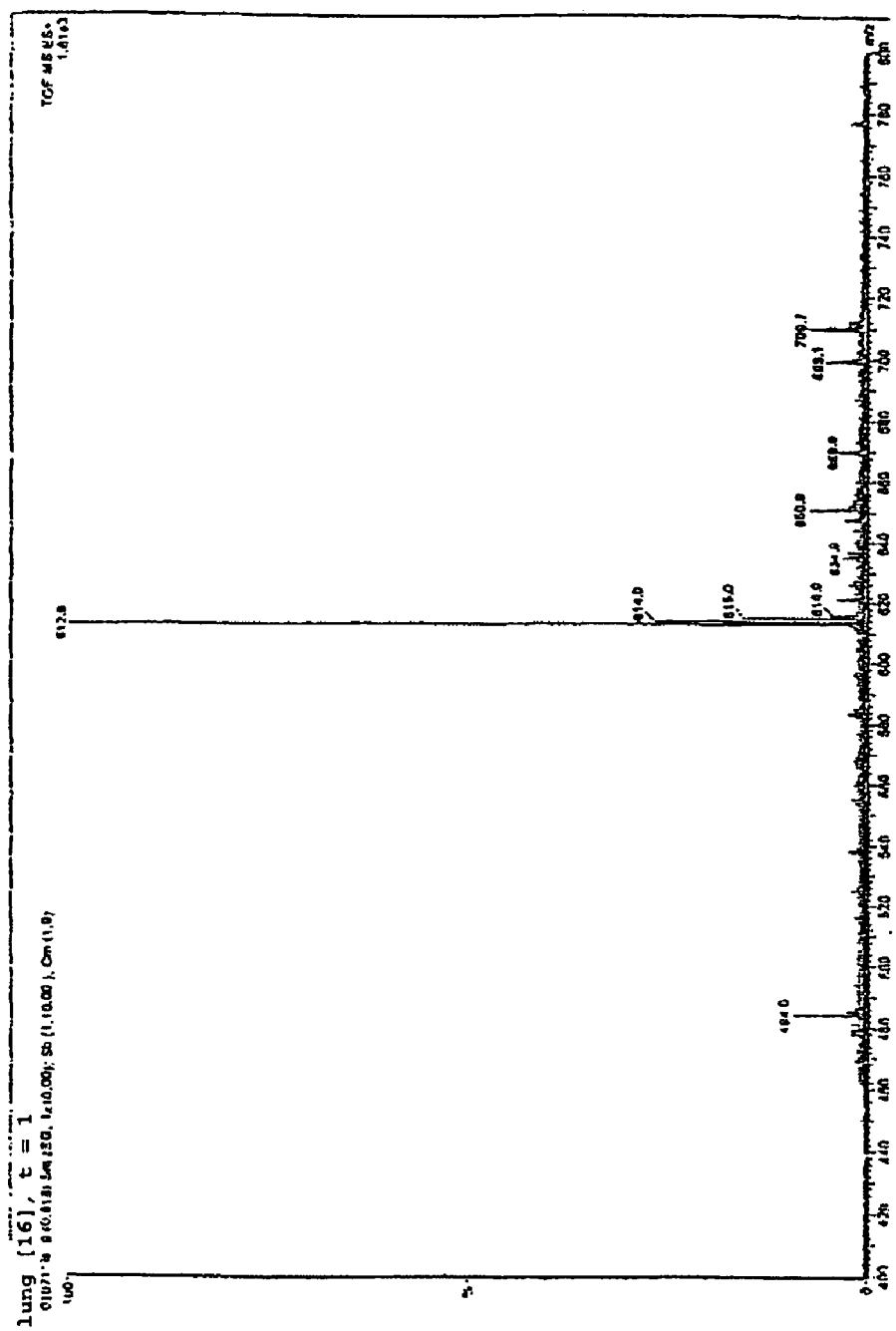
Figure 8:
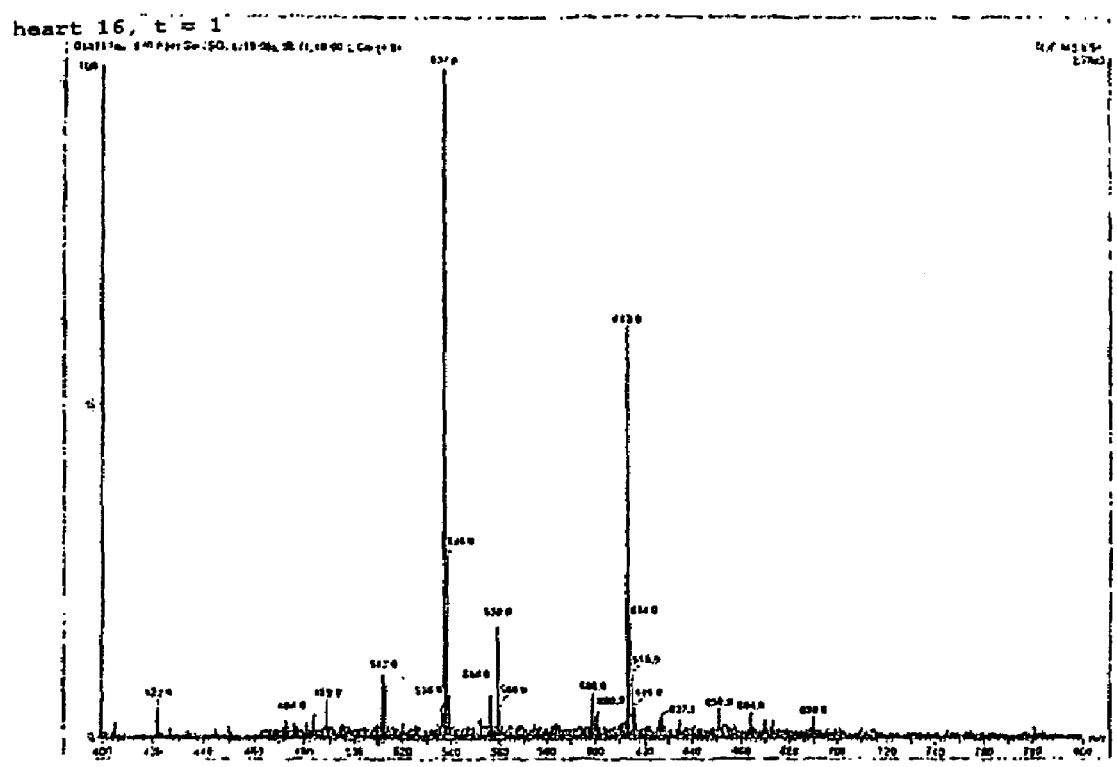

These results are illustrated in FIGS. 6 to 8.

FIG. 6 represents a mass spectrum of the renal extract, in which the presence of many peaks characteristic of phosphinic peptides is observed (to be compared with FIG. 2).

FIG. 7 represents a mass spectrum of the lung extract, in which an absence of peaks characteristic of phosphinic peptides is observed.

FIG. 8 represents a mass spectrum of the heart extract, in which an absence of peaks characteristic of phosphinic peptides is observed.

However, it is observed that the results obtained by mass spectrum analysis and by HPLC are divergent; in fact, the presence of peaks characteristic of phosphinic peptides is detected by HPLC in the extracts originating from the lungs and from the heart. This dichotomy comes from the fact that, in mass spectrometry, the mass peaks which may correspond to the products being sought can be masked by the mass peaks originating from the endogenous compounds contained in the organs, which are still present after the extraction steps. On the basis of these results, tandem MS/MS fragmentation mass spectrometry is systematically carried out in order to demonstrate the presence of phosphinic peptides in the various extracts.

This MS/MS mass spectrometry makes it possible to fragment a peptide at a given mass and therefore to reveal, in the MS/MS spectrum, only the fragments of such a peptide (spectral signature). These experiments therefore prove to be much more effective for demonstrating the presence of a product, even if this product does not appear in the MS spectrum.

Figure 9:
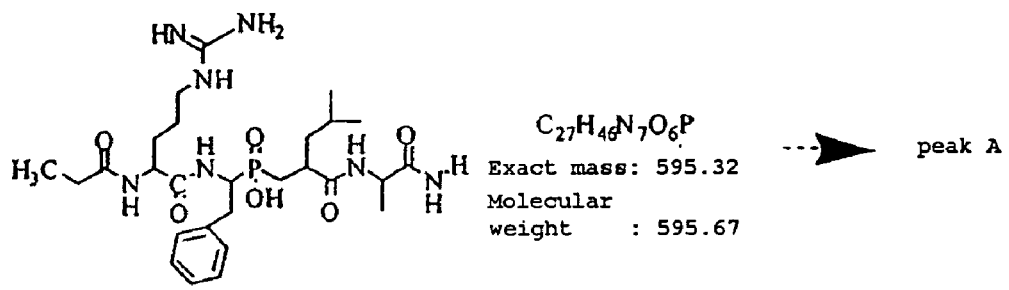
FIGS. 9 and 10 represent the fragments obtained when the peptide propyl-$^3$H-Arg-Phe(PO$_2$—CH$_2$)Leu-Ala-NH$_2$ is subjected to an MS/MS spectrum.
Figure 9:
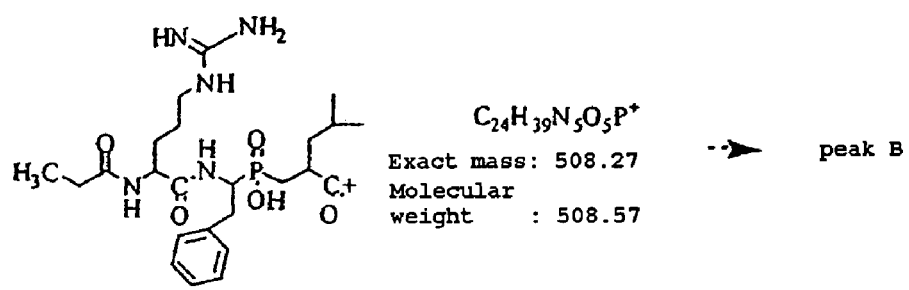
Figure 9:
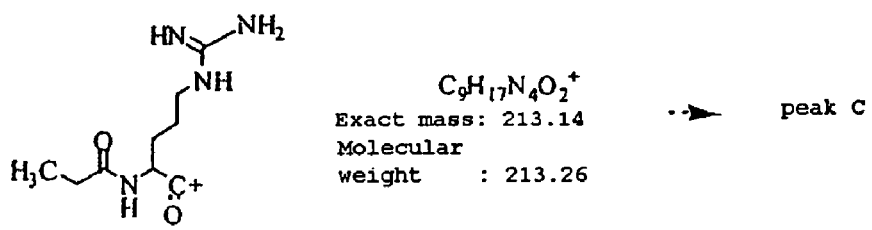
Figure 9:
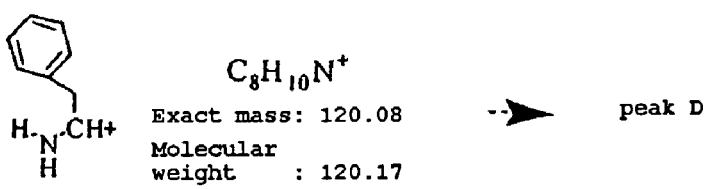
Figure 10:
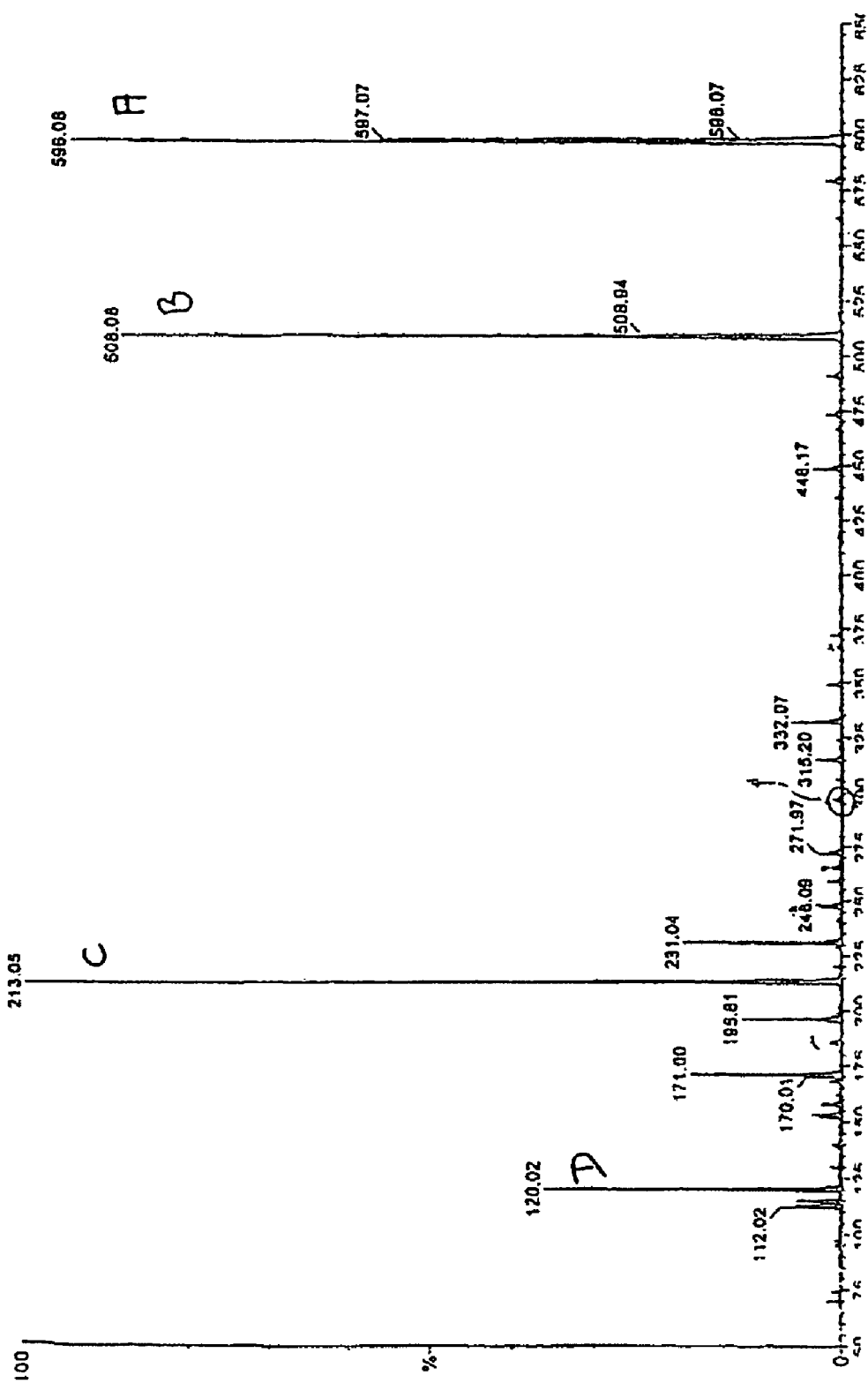
Figure 11:
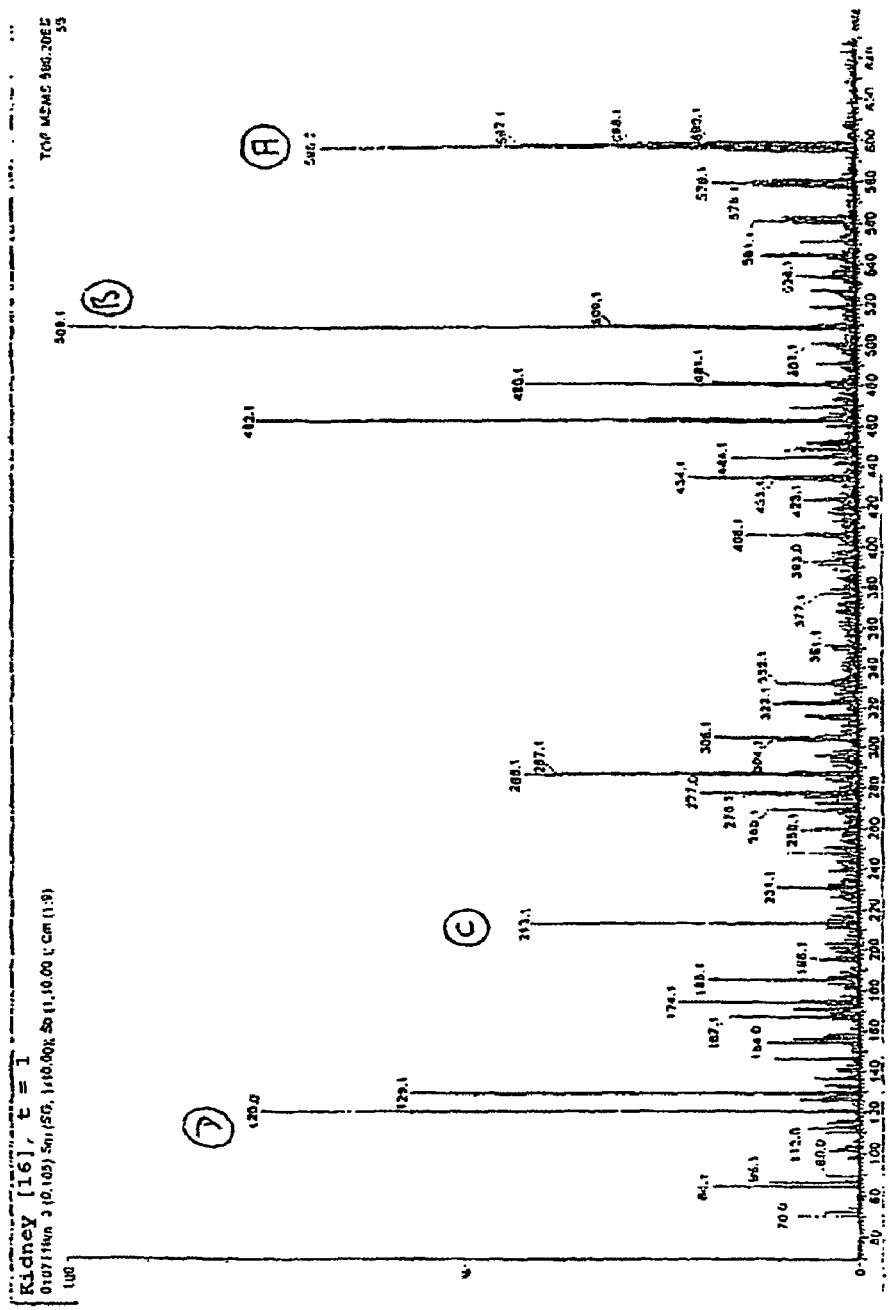
FIGS. 11 to 13 illustrate the fragmentation peaks obtained from the kidney, lung and heart extracts in an MS/MS fragmentation experiment, selecting the product of mass at 595. These figures demonstrate the presence of the product propyl-NH-Arg-Phe(PO$_2$—CH$_2$)Leu-Ala-NH$_2$ in these three organ extracts.
Figure 12:
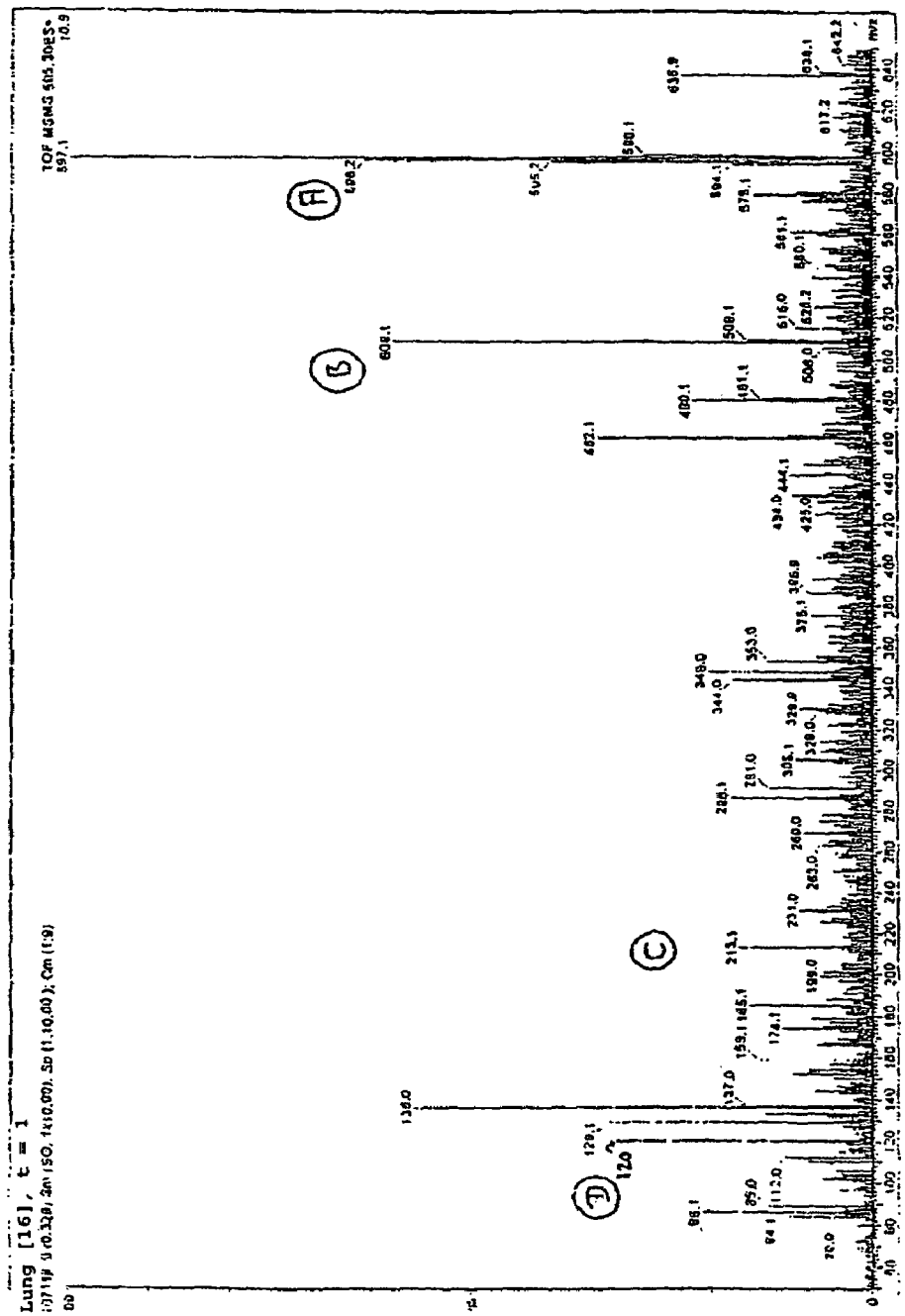
Figure 13:
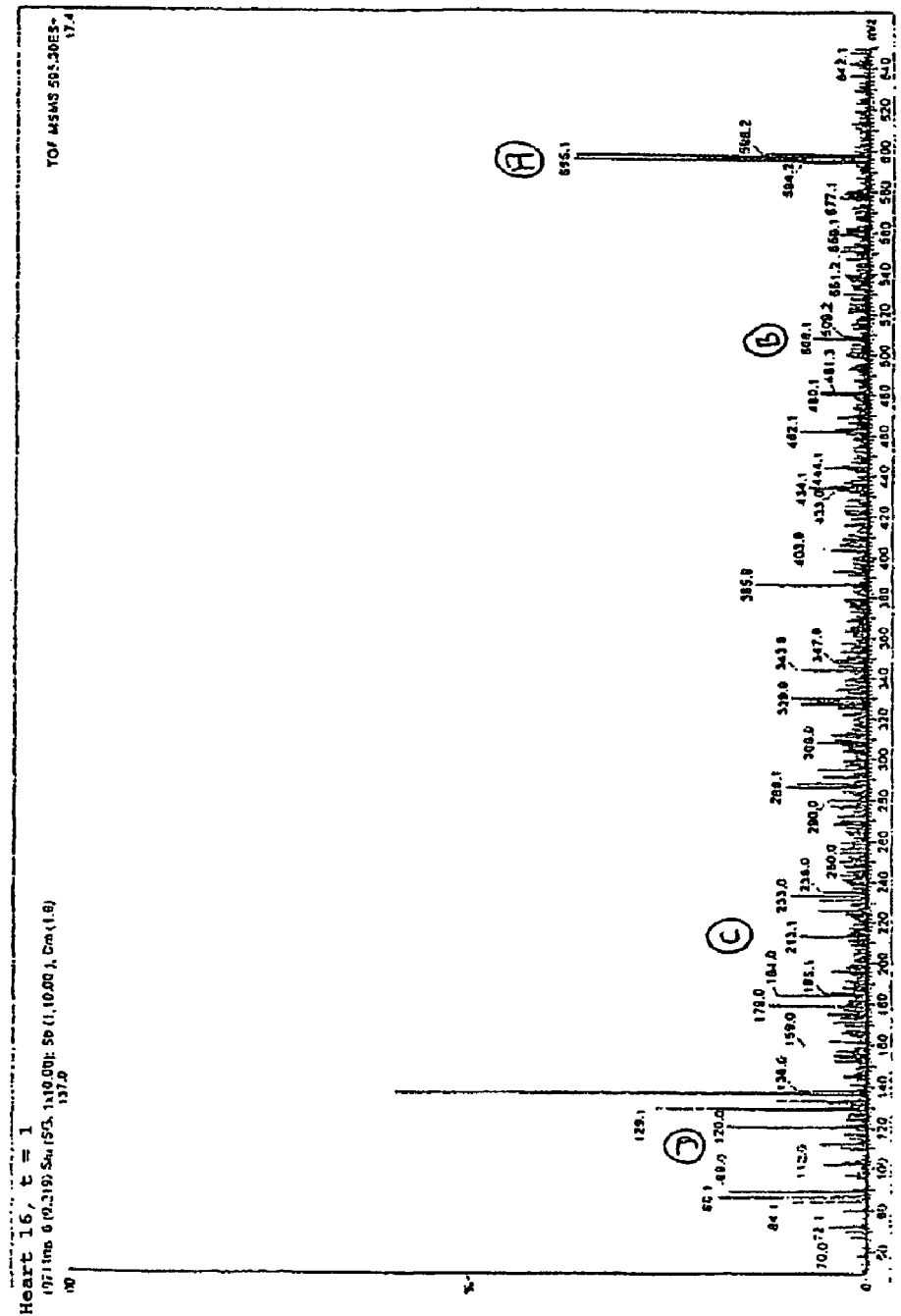
Figure 14:
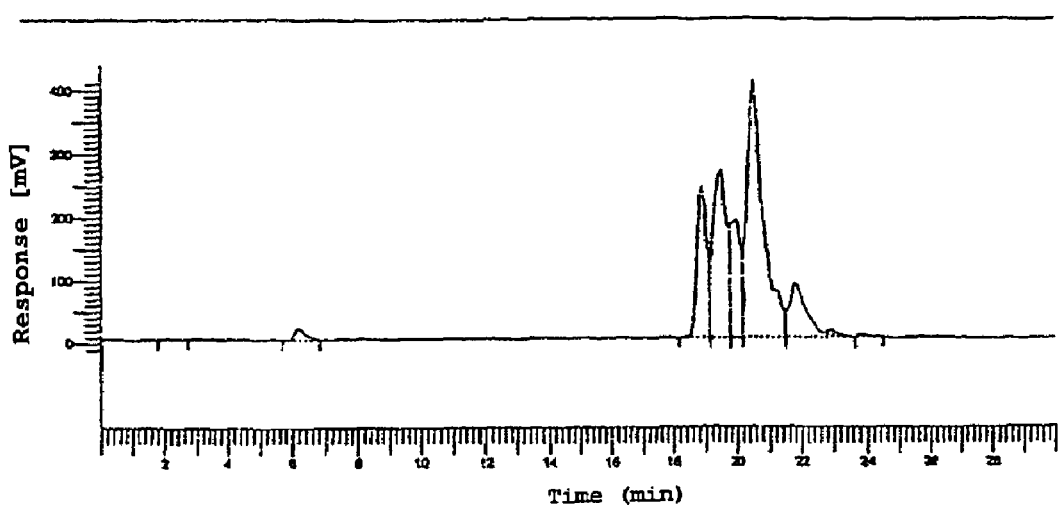
FIGS. 14 to 19 illustrate HPLC spectra corresponding to the peptide propyl-$^3$H-Arg-Phe(PO$_2$—CH$_2$) Leu-Ala-NH$_2$ in pure form (4 diastereoisomers, FIG. 13) and then in the various organ extracts (lung, heart, liver, kidney and brain)
Figure 15:
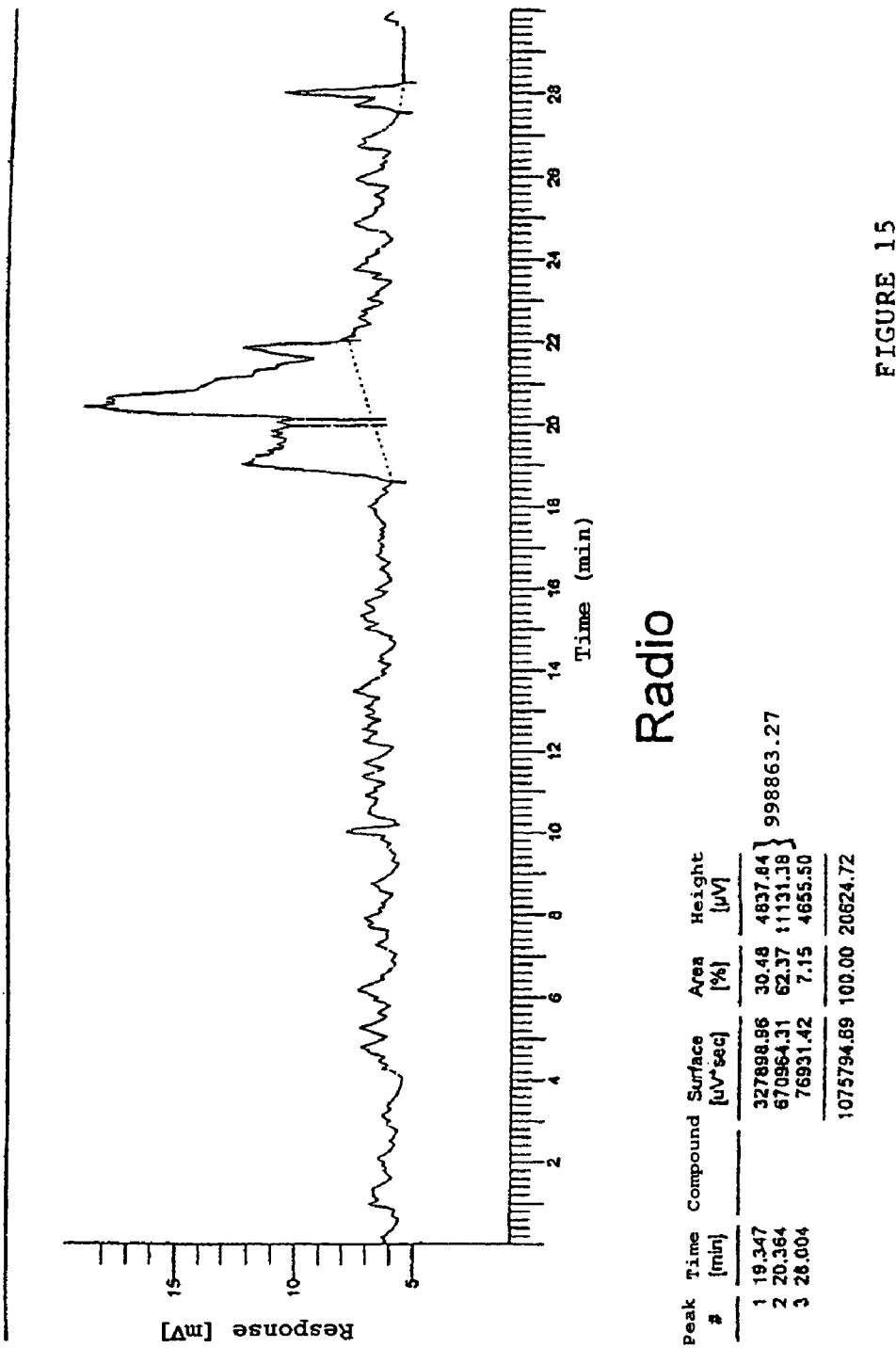
Figure 16:
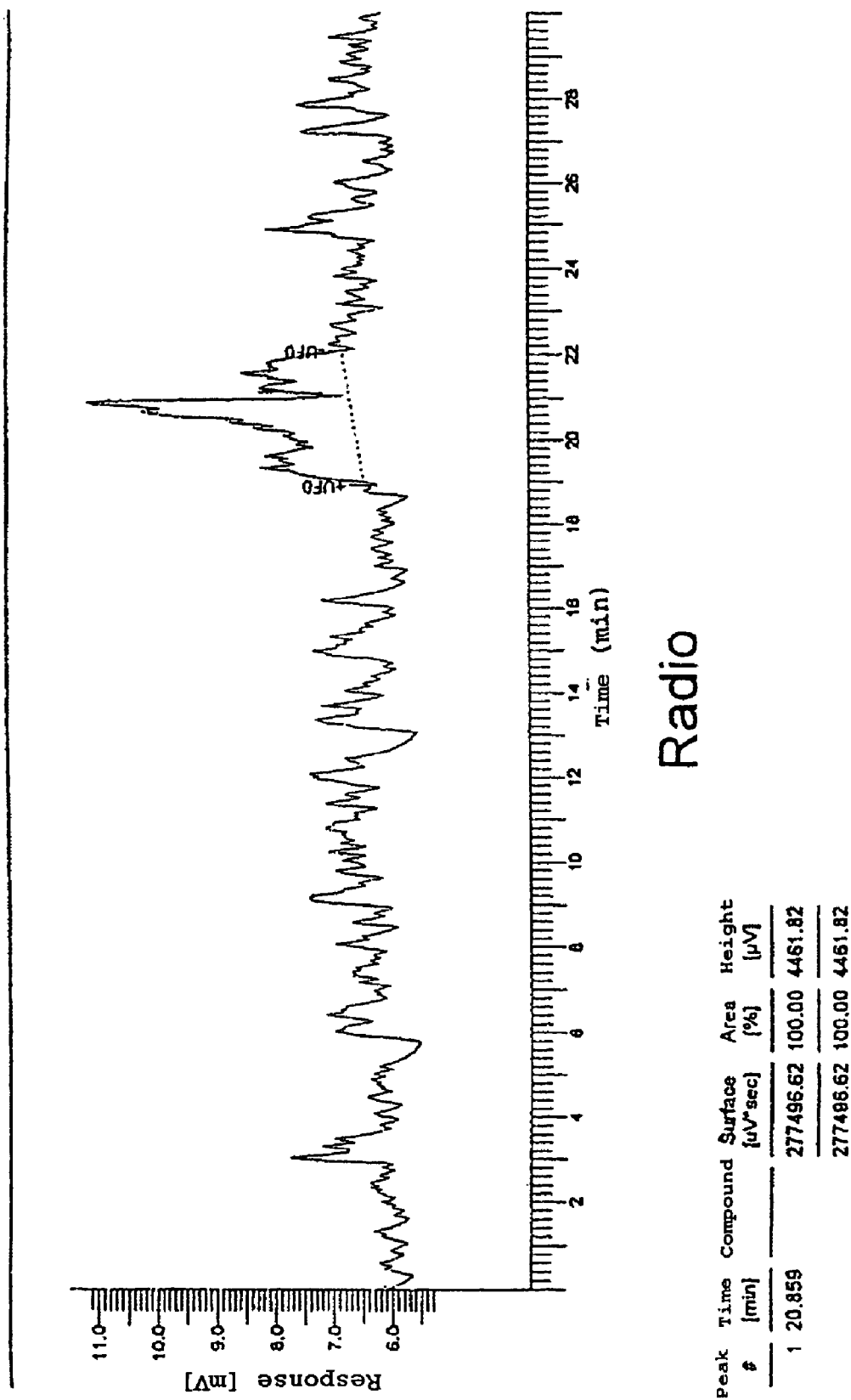
Figure 17:
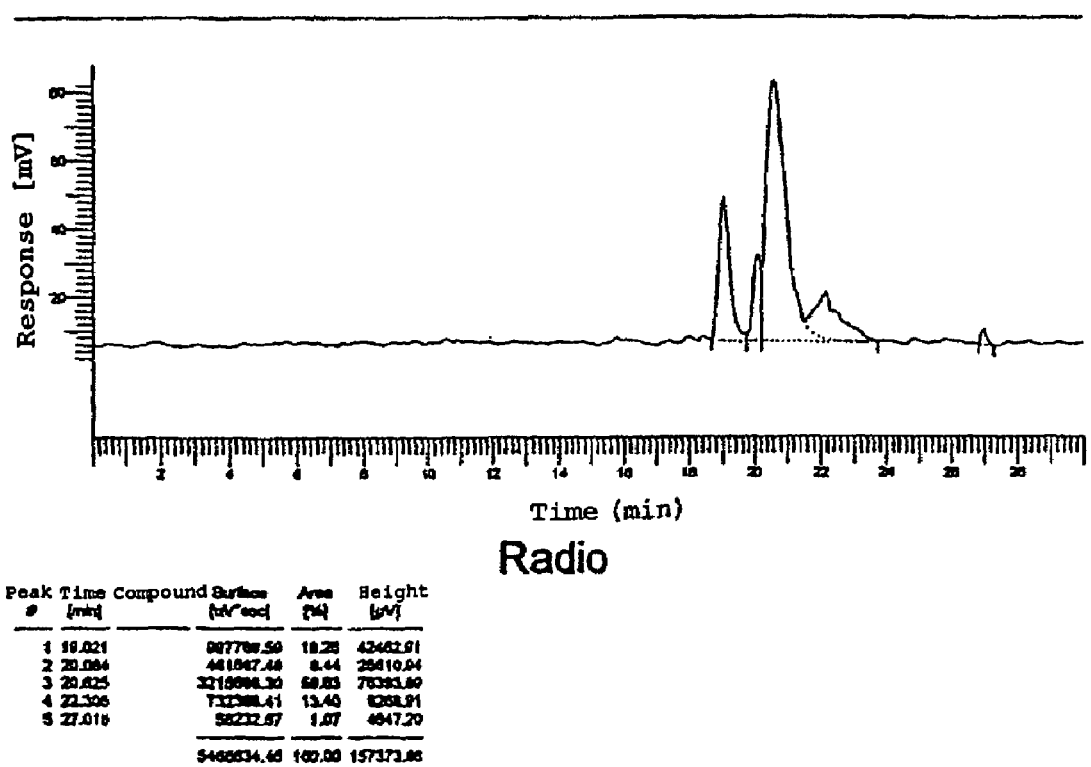
Figure 18:
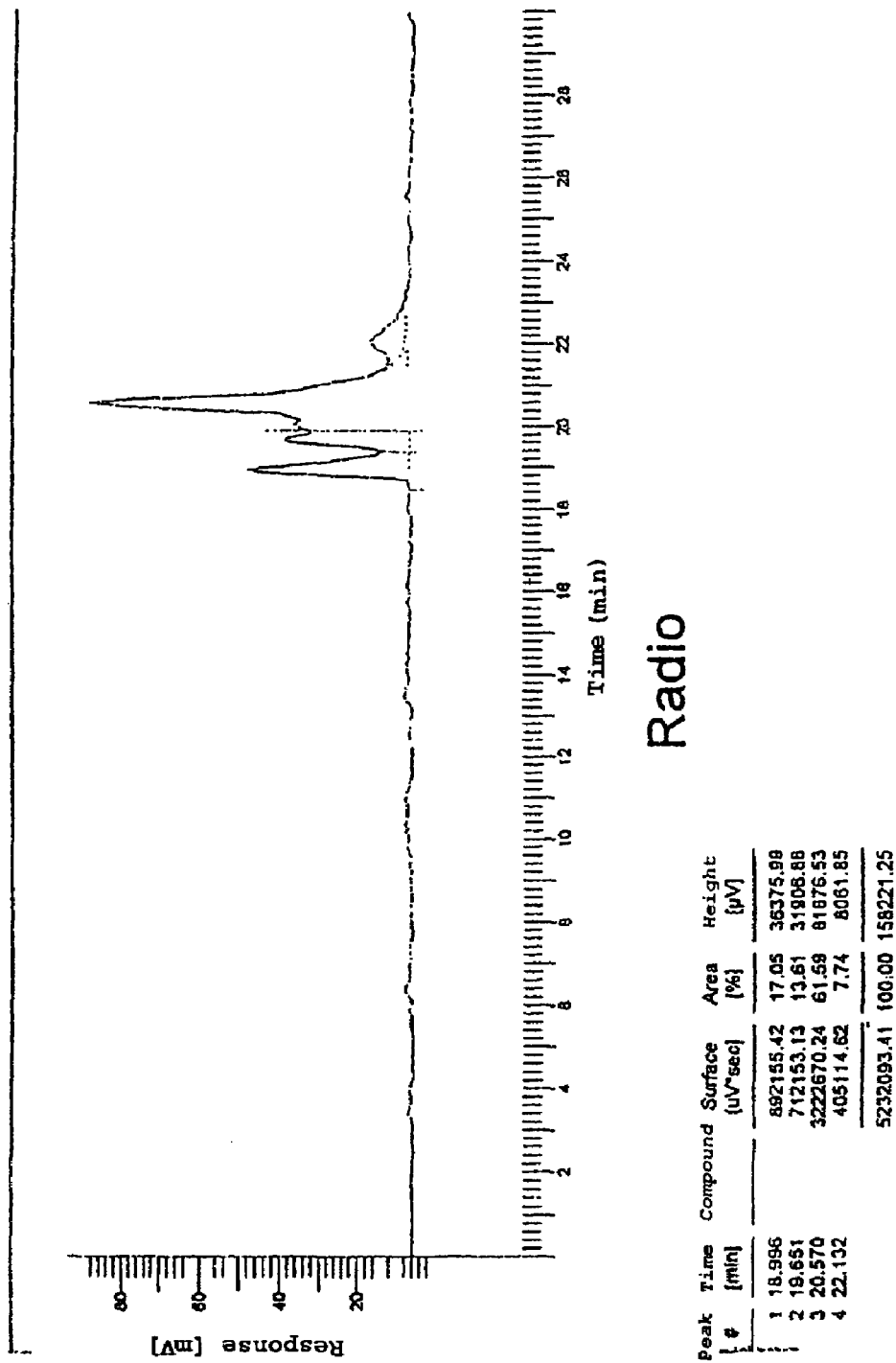
Figure 19:
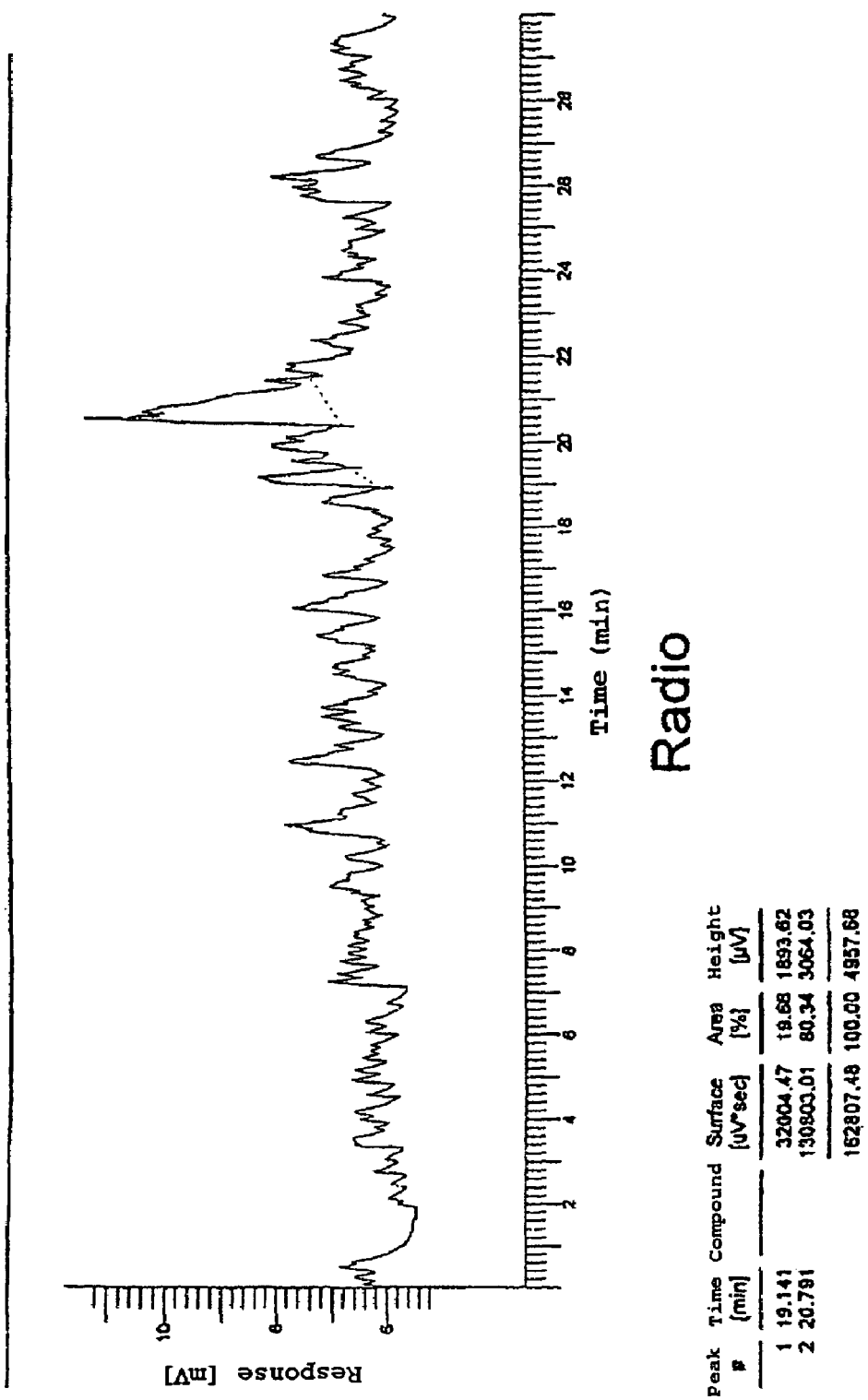

This MS/MS mass spectrometry made it possible to identify the presence of a phosphinic peptide in the lungs and the heart, i.e. propyl-Arg-Phe($PO_2$—$CH_2$)Leu-Ala-$NH_2$. This peptide also appears in the kidney and in the liver; however, in these organs, other phosphinic peptides are also observed. FIGS. 9 and 10 represent the fragments obtained when the peptide propyl-Arg-Phe($PO_2$—$CH_2$)Leu-Ala-$NH_2$ is subjected to an MS/MS spectrum. Observation of the fragmentation peaks characteristic of the peptide propyl-Arg-Phe($PO_2$—$CH_2$)Leu-Ala-$NH_2$ in the kidney (FIG. 11), lung (FIG. 12) and heart (FIG. 13) extracts makes it possible to conclude that this peptide is present in these organs.

The selection of the product propyl-Arg-Phe($PO_2$—$CH_2$)Leu-Ala-$NH_2$ by means of this approach for screening a peptide library led to this peptide being prepared in pure form in order to establish in detail its tissue distribution properties.

The study of the tissue distribution of the radiolabeled propyl-Arg-Phe($PO_2$—$CH_2$)Leu-Ala-$NH_2$ peptide, injected in pure form, shows that this compound is effectively capable of being distributed in various tissues, in mice (20 mg/kg, 100 µCi, mouse then sacrificed 1 h after the I.P. injection of the product), as attested by the images of the various organs, obtained by autoradiography; this product is observed in the heart, the brain, the liver, the lungs and the kidneys. Very advantageously, it is observed that this peptide is capable of crossing the blood-brain barrier, since it is observed in the brain. The same procedures for extraction and structural analysis demonstrate that all the radioactivity observed by autoradiography corresponds to the presence of the peptide propyl-Arg-Phe($PO_2$—$CH_2$)Leu-Ala-$NH_2$ in intact form (FIG. 20).

FIGS. 14 to 19 represent HPLC spectra, with detection of radioactivity, corresponding to the pure tritiated product propyl-Arg-Phe($PO_2$—$CH_2$)Leu-Ala-$NH_2$, and to the various organ extracts originating from a mouse that was administered the peptide propyl-Arg-Phe($PO_2$—$CH_2$)Leu-Ala-$NH_2$ (20 mg/kg, 100 µCi) and was sacrificed 1 h after injection of the product.

In order to illustrate the ability of the peptide propyl-Arg-Phe($PO_2$—$CH_2$)Leu-Ala-$NH_2$, firstly, to target certain organs such as the heart and the lungs and, secondly, to accumulate in these organs, another molecule was used under the same conditions as a negative control; it is another molecule of the library described above, i.e. propyl-Tyr-Phe($PO_2$—$CH_2$)Leu-Pro-$NH_2$.

The study of its tissue distribution, under the same experimental conditions as those used for the compound propyl-Arg-Phe($PO_2$—$CH_2$)Leu-Ala-$NH_2$ shows that the compound propyl-Arg-Phe($PO_2$—$CH_2$)Leu-Ala-$NH_2$ distinguishes itself very clearly from the peptide propyl-Tyr-Phe($PO_2$—$CH_2$)Leu-Pro-$NH_2$ both in terms of its ability to accumulate in the heart and the lungs, and in terms of its ability to appear in the brain.

FIG. 21 represents autoradiography images of various organ sections prepared from a mouse that was administered the peptide propyl-Tyr-Phe(PO$_2$—CH$_2$)Leu-Pro-NH$_2$ (20 mg/kg, 100 µCi) and was sacrificed 1 h after injection of the product.

EXAMPLE 2

Properties and Identification of the Potential Targets of the Phosphinic Peptide Propyl-NH-Arg-Phe (PO$_2$—CH$_2$)Leu-Ala-NH$_2$ The specific tissue distribution of the phosphinic peptide propyl-NH-Arg-Phe(PO$_2$—CH$_2$)Leu-Ala-NH$_2$, in particular in the brain, led to the hypothesis being put forward that this compound could interact with zinc peptides of the angiotensin I-converting enzyme (ACE) and/or neutral endopeptidase (NEP, neprilysin) type. In fact, in general, phosphinic peptides have the ability to interact specifically with zinc proteases or peptidases (see French patent application No. 98 08464); in addition, these two zinc peptidases are known to have tissue distributions that are compatible with that observed for the phosphinic product propyl-NH-Arg-Phe (PO$_2$—CH$_2$)Leu-Ala-NH$_2$ (Cadwell et al., Science, 1975, 191, 1050-1051; Roques et al., Tips, 1990, 11, 245-249).

For this reason, the inhibitory capacity of the phosphinic peptide propyl-NH-Arg-Phe(PO$_2$—CH$_2$)Leu-Ala-NH$_2$ was evaluated with respect to the purified forms of these two peptidases (measurement of the Ki values according to Dive et al., PNAS, 1999, 96, 4330-4335). As shown in FIGS. 22 and 23, this peptide has IC$_{50}$ values equal to 30 nM and 100 nM, respectively, with respect to angiotensin-converting enzyme and NEP, corresponding to inhibition constant Ki values of 15 nM and 30 nM. This compound therefore behaves as an extremely potent inhibitor with respect to these two peptidases.

Since these two peptidases are considered to be relatively nonselective, it may appear to be surprising that, after the in vivo screening, only the peptide propyl-NH-Arg-Phe(PO$_2$—CH$_2$)Leu-Ala-NH$_2$ was identified by this screening method.

In order to have a better knowledge of the inhibitory properties of the various molecules contained in the starting library, with respect to ACE and NEP, the inhibitory capacity of sublibraries containing discrete mixtures of generic formula:

propyl-NH-Aaa-Phe (PO$_2$—CH$_2$)Leu-Yaa-NH$_2$ in which the position marked as Aaa contains a specific amino acid, whereas, in position Yaa, a mixture of 20 natural acids occurs, was evaluated.

FIG. 24 gives the percentage inhibition of the mixtures of phosphinic peptides, corresponding to the generic formula above, with respect to ACE, according to the nature of the residue at position Aaa. The results reported in this figure indicate very clearly that many phosphinic peptides present in these sublibraries appear to be potent inhibitors of ACE. Advantageously, it is seen that, among the residues at position Aaa that optimize the inhibitory capacity of the compounds with respect to ACE, are the residues His, Arg and Tyr.

When the same sublibraries are tested on NEP (FIG. 25), it also appears that many peptides contained in the sublibraries should behave as very potent inhibitors of NEP. It will be noted that several types of amino acid at position Aaa optimize the enzyme-inhibitor interactions.

On the basis of these in vitro data, it is clear that the product propyl-NH-Arg-Phe(PO$_2$—CH$_2$)Leu-Ala-NH$_2$ definitely does not correspond to the most potent inhibitor in vitro, contained in the library, with respect to these two peptidases.

This clearly shows the advantage of the method according to the invention; in fact, on the basis of only the in vitro screening, it is impossible to select, for example, the only compound that is in fact effective; specifically, using the in vitro test, many compounds of the library, having the ability to act as potent inhibitors, are selected, whereas the method according to the invention, which includes an in vivo step, will be much more selective insofar as only the compound capable of acting in vivo is thus selected.

On the basis of the ability of the compound propyl-NH-Arg-Phe(PO$_2$—CH$_2$)Leu-Ala-NH$_2$ to potently inhibit ACE and NEP peptidases in vivo, the applications of such a product in cardiovascular pathologies can be expected.

The metabolic stability of the compound propyl-NH-Arg-Phe(PO$_2$—CH$_2$)Leu-Ala-NH$_2$ and its very good tissue distribution, in particular in regions known to express these two zinc peptidases, lead to the prediction that this product will have an excellent capacity for inhibiting these two peptidases in vivo. Consequently, such a product will find important applications in cardiovascular pathologies in humans.

EXAMPLE 3

Importance of the Combination of Steps (2) and (3) to (5) in the Method According to the Invention Reminder of the Method According to the Invention After injection of a library of compounds radiolabeled with tritium into animals, the method according to the invention comprises the analysis of the tissue distribution of the radioactivity of the molecules administered, using a biological sample, and more particularly sections of tissues or organs from which samples were taken, by means of the detection of a radioactive signal on said frozen tissue or organ sections, using a suitable radioimaging device.

Insofar as only the organs or tissues exhibiting a radioactive signal are subsequently analyzed in order to establish the identity of the compound(s) present in the tissue under consideration, the sensitivity of the method used for detecting the radioactive signal plays a central role here.

Comparison of the Relative Sensitivity of Tritium Radioimaging and of Mass Spectrometry In order to establish this comparison, 500 µg of a tritium-radiolabeled phosphinic compound propyl-Arg-Phe(PO$_2$—CH$_2$)Ala-Ala-NH$_2$ (pro-Arg) (specific radioactivity of 68 mCi/mmol) were injected into mice. One hour after injection of the product, its tissue distribution was studied by detection of the radioactivity using frozen tissue sections. The organs containing radioactivity were treated in order to prepare tissue extracts which could enable their analysis by mass spectrometry, in accordance with the extraction protocol illustrated in FIG. 26. Comparison of the ability of these two methods to detect the presence of the phosphinic compound injected into the animals makes it possible to show that it is the combination of the steps of the method according to the invention which makes it possible to solve the problem of the detection and the identification of radioactive compounds present in organs or tissues, using a library of diverse radioactive molecules.

Kidney (FIG. 27):

β-imager: the radiograph indicates the presence of the radiolabeled compound in this organ (in these images, the maximum and minimum intensity of radioactivity are represented, respectively, in dark grey and light grey).

Based on the integration of the signal and of the specific radioactivity of the product (68 mCi/mmol), it is possible to determine the amount of product present per mm² of kidney.

On the section, the radioactive signal observed is 14.5 pCi/mm², representing 0.2 pmol/mm² of product (127 pg/mm²). By integrating this amount over the volume of a whole kidney, it is possible to determine that the total amount of product present in the kidney corresponds to 15% of the injected dose (75 μg).

Mass: the product is extracted from ground kidney material originating from an animal treated under the same conditions as above (extraction protocol described in FIG. 26), followed by concentration of the fractions to dryness and taking up the product in 100 μl of solvent (water/formic acid; 50:50); if the extraction was quantitative, the theoretical concentration of the sample should be of the order of 1.5 mM. Based on this working hypothesis, it can be estimated that the injection of a microliter of this 100-fold diluted solution (15 μM) represents 15 pmol of product introduced into the mass spectrometer (Electrospray, Quatro, Micromass).

This amount is entirely compatible with the sensitivity of mass spectrometry.

FIG. 27 confirms in fact that it is entirely possible to observe the presence of the product in this sample, characterized by a peak of mass corresponding to a molecular weight of 596 Daltons (M+H). On this mass spectrum, compared with the other signals, the peak at 596 Da has the greatest intensity, which makes it possible to conclude that the phosphinic peptide injected is largely in the majority compared to the endogenous products co-extracted with this product. The chemical identity of the product is confirmed by observing the fragments A, B and C, when the sample is switched into MS/MS mode, allowing this compound to be fragmented. The same peaks A, B and C are observed when the pure product is fragmented.

Lung (FIG. 28):

β-imager: the radiograph indicates a smaller amount of the product in the lung: 2.6 pCi/mm² of radioactivity in this organ compared with 14.5 pCi/mm² in the kidney, i.e. 2.2% of the injected dose.

Mass: a solution of the lung sample at a theoretical concentration of 22 μM was subjected to a mass analysis. The injection of one microliter of this sample, compared to the experiment carried out in the kidney, could imply a very good observation of the product pro-Arg. The MS spectrum of FIG. 28 indicates that this lies within the limits of detection, the signal corresponding to pro-Arg being of the order of the noise observed in this spectrum. However, by means of fragmentation (MS/MS experiments), it is possible to conclude that the product is present, the expected fragments (A, B and C) being clearly observed in the MS/MS spectrum.

Brain (FIG. 29):

β-imager: the radiograph indicates very weak radiolabeling in a very localized region of the brain: 0.35 pCi/mm² compared with 14.5 pCi/mm² in the kidney. This time, since the volume of brain involved in the radiolabeling is not precisely determined, the total amount of product present in the brain is more problematic to estimate.

Mass: after extraction of the product from the brain, injection of the entire fraction liable to contain our product into the spectrometer did not make it possible to observe a peak at 596. The fragmentation experiments make it possible to detect peaks A, B and C, and therefore confirm the presence of the intact product in the brain. However, these experiments are at the limit of the threshold of detection.

The results illustrated in FIGS. 27 to 29 demonstrate the role of the radioimaging device/mass spectrometry combination in detecting a radiolabeled phosphinic peptide within a tissue. In fact, in the case of the brain (FIG. 29), it may be noted that the mass spectrometry alone was at the limit of detection, whereas the presence of the phosphinic peptide is revealed by the radioimaging device; these data show the necessity of combining a step for detection of the radioactive products, in the organs or the tissues, using a radioimaging device for the most sensitive detection of said radioactive products, followed by a step of analysis by mass spectrometry, making it possible to establish the chemical identity of the products detected in the brain by means of the radioimaging.

In fact, although it is very effective, mass spectrometry requires, according to the nature of the tissue, absolute purification of a very small amount of the product, which constitutes an objective that is extremely difficult to achieve given the presence of a very large amount of endogenous products contained in the various organs. The presence of endogenous products, in the range of masses concerned for the products injected (200-800 Da), has another very important consequence on the relative sensitivity of the mass spectrometry. The sensitivity of the mass spectrometry is in fact conditioned by the purity of the samples to be analyzed. The presence of salts or of other impurities in the sample to be analyzed can bring about a decrease of several orders of magnitude in the theoretical sensitivity of the mass spectrometry.

The use of a step for detecting a radioactive signal, which does not require any treatment aimed at isolating the products that it is desired to identify, by means of a suitable radioimaging device, which enables the detection of these products in an optimal manner, combined with a step of fine analysis of the radioactive products thus selected, makes it possible to obtain the desired performance levels from the point of view of the sensitivity of detection of the products in the various organs or tissues.

EXAMPLE 4

Analysis of the Tissue Distribution of Mixtures of Compounds Radiolabeled with Fluorine 18, by Positron Emission Tomography (Presence of a Step (1') According to the Invention)

Materials and methods:

Animals: the experiments were carried out on Wistar rats weighing 200 g (Janvier) fed ad libitum and housed in a conventional animal house (controlled atmosphere, day/night period 12/12). The rats are anesthetized with a 3.5% isoflurane in $O_2$ gas mixture for the induction phase and maintained at 2% of anesthetic during the entire acquisition. The injection of the mixture (for the co-injections) of the various tracers is carried out intravenously in the form of a bolus of 300 μl over a period of time of less than 30 seconds for the four animals.

PET: four rats are positioned in an EXACT HR+ camera (Siemens) (63 simultaneous contiguous sections, resolution in two-dimensional mode measured at 1 cm from the center, of 4.5 mm in the transverse direction and 4.1 mm in the axial direction). The correction of attenuation of the tissues and of the support for gamma rays of 511 keV is obtained by means of a transmission scan with $^{68}$Ge-$^{68}$Ga sources (15 min). The dynamic analysis after injection of the tracers is carried out by acquisition of 102 frames (25×0.2 min; 19×0.3 min; 20×0.5 min; 38×1 min).

Tracers: [$^{18}$F]FDG is a metabolic marker for glucose consumption; [$^{18}$F]F-A85380 is an $\alpha_2\beta_4$ nicotinic agonist. Two rats are given the mixture (1:1) of the two tracers, while two other rats are given just one of the two tracers. For all the animals, the total dose administered by rapid IV (bolus) is $1.4 \times 10^7$ Bq, in aqueous solution in a volume of 400 μl.

Data analysis: the regions of interest are traced by means of the CAPP software and the concentrations of radioactivity are expressed in Bq per ml of tissue.

Results:

The positron emission tomography after injection of mixtures of radioactive products into an animal makes it possible to rapidly search for the presence, in such mixtures, of products capable, for example, of reaching the brain or even the heart; on the basis of such a criterion, it is possible to rapidly sort mixtures in order to select only those which satisfy the selected tissue distribution criteria.

This step, combined with the other steps of the method, thus makes it possible to detect radiolabeled products with a very low threshold of detection.

The invention claimed is:

1. A method of screening molecules, comprising:
   (1) administering to at least one animal molecules, wherein the molecules have the following general formula: propyl-NH-Yaa-(R,S)Phe(PO$_2$—CH$_2$)(R,S)Leu-Yaa'-NH$_2$, wherein each of Yaa and Yaa' represents a natural amino acid, in which each molecule is pre-labeled with a radioactive isotope capable of being detected,
   (2) sacrificing at least one of the animals and analyzing in vivo the distribution within tissues or organs of said at least one animal of the radioactivity of the molecules administered by analyzing sections of tissues or organs from which samples have been taken with an imaging devices capable of detecting said radioactive isotope,
   (3) selecting sections of tissues or organs in which a radioactive signal is detected,
   (4) isolating from said sections of tissues or organs, selected in step (3), radioactive fractions, and
   (5) identifying a molecule from the administered molecules, using the radioactive fractions obtained in step (4), distributed in a particular tissue and/or organ.

2. The method as claimed in claim 1, wherein, during administering, radioactive molecules are injected into the animal.

3. The method as claimed in claim 1, wherein, prior to step (2), said method comprises a step (1') for analyzing the tissue distribution of the radioactivity of the molecules administered, by subjecting at least one of the animals to external imaging, by means of detection devices, incorporating cameras suitable for detecting the particles emitted by the radioactive isotope selected.

4. The method as claimed in claim 1, wherein the radioactive isotopes are selected from the group consisting of tritium ($^3$H), carbon 14 ($^{14}$C), carbon 11 ($^{11}$C), iodine 131 ($^{131}$I), iodine 125 ($^{125}$I), iodine 124 ($^{124}$I), iodine 123 ($^{123}$I), phosphorus 32 ($^{32}$P), fluorine 18 ($^{18}$F), sulfur 35 ($^{35}$S), technetium 99 ($^{99m}$Tc), indium 113 ($^{113}$In), copper 64 ($^{64}$Cu), bromine 76 ($^{76}$Br), nitrogen 13 ($^{13}$N) and oxygen 15 ($^{15}$O).

5. The method as claimed in claim 1, wherein, in step (2), distribution within the tissues or organs of said at least one animal of the radioactivity is visualized by means of detection devices, incorporating imaging devices suitable for detecting the particles emitted by the radioactive isotope selected.

6. The method as claimed in claim 1, wherein the radioactive molecules are injected in the form of a mixture.

7. The method as claimed in claim 1, wherein, prior to administering, said labeled molecules are prepared by:
   synthesizing a mixture of said molecules using at least one chemical or enzymatic pathway, and
   labeling said molecules with said radioactive isotopes.

8. The method as claimed in claim 1, wherein steps (1) to (5) are carried out simultaneously on several animals, for which the amounts administered in step (1) are different for different animals, and where the analysis of the distribution of the radioactivity of the molecules, according to step (2), is carried out at different times upon different animals.

9. The method as claimed in claim 1, wherein the isolation of the radioactive molecule(s), associated with said organ(s), according to step (4), is carried out in accordance with the following steps:
   removal of the tissues or organs in which radioactivity has been detected,
   grinding of said tissues or organs in a suitable buffer,
   centrifugation of each ground material and recovery of a supernatant,
   filtration of said supernatant,
   adjustment of the pH of said supernatant, and
   separation by fractions and recovery of the radioactive fractions of said supernatant.

10. The method as claimed in claim 1, wherein, in step (5), the identifying is conducted by mass spectrometry combined with a tandem mass spectrometry (MS/MS) analysis.

11. The method as claimed in claim 1, wherein the molecules, according to step (1), have the following general formula: propyl-$^3$H—NH-Yaa-$_{(R,S)}$Phe(PO$_2$—CH$_2$)$_{(R,S)}$Leu-Yaa'-NH$_2$, in which Yaa and Yaa' represent positions in which the 20 natural amino acids occur.

* * * * *